(12) United States Patent
Yu et al.

(10) Patent No.: US 10,624,847 B2
(45) Date of Patent: Apr. 21, 2020

(54) DECOMPOSABLE APPARATUS AND METHODS FOR FABRICATING SAME

(75) Inventors: Chris C Yu, Conneautville, PA (US); Xuedong Du, Shanghai (CN)

(73) Assignee: AnPac BioMedical Science Co., Ltd., Tortola (VG)

( * ) Notice: Subject to any disclaimer, the term of this patent is extended or adjusted under 35 U.S.C. 154(b) by 1680 days.

(21) Appl. No.: 13/196,622

(22) Filed: Aug. 2, 2011

(65) Prior Publication Data

US 2013/0035632 A1    Feb. 7, 2013

(51) Int. Cl.
| | | |
|---|---|---|
| A61K 9/00 | (2006.01) |
| A61M 37/00 | (2006.01) |
| A61M 31/00 | (2006.01) |
| A61M 39/02 | (2006.01) |

(52) U.S. Cl.
CPC ......... *A61K 9/0097* (2013.01); *A61M 31/002* (2013.01); *A61M 37/00* (2013.01); *A61M 39/0208* (2013.01)

(58) Field of Classification Search
CPC .................................................. A61K 9/0097
See application file for complete search history.

(56) References Cited

U.S. PATENT DOCUMENTS

| | | | | |
|---|---|---|---|---|
| 5,641,745 A * | 6/1997 | Ramtoola | ............ | A61K 9/1647 424/474 |
| 2003/0095998 A1* | 5/2003 | Pourdeyhimi | ........... | A61K 9/70 424/443 |
| 2011/0190795 A1* | 8/2011 | Hotter | .................. | A61F 2/0063 606/151 |

OTHER PUBLICATIONS

Kenawy et al (Release of tetracycline hydrochloride from electrospun poly(ethylene-co-vinylacetate), poly(lactic acid), and a blend, Journal of Controlled Release 81 (1-2) (2002) pp. 57-64).*
Kim et al (Microneedles for drug and vaccine delivery, Advanced Drug Delivery Reviews 64(2012) (Year: 2012).*
Betancourt et al (Int J Nanomedicine, 2006, 1(4), 483-495). (Year: 2006).*

\* cited by examiner

*Primary Examiner* — Benjamin J Packard
(74) *Attorney, Agent, or Firm* — Weisun Rao; Jun Chen; Venture Partner, LLC

(57) ABSTRACT

The invention provides decomposing apparatus which comprises a first sub-component and a first micro device comprising a decomposable material, wherein the sub-component comprises a drug, a medical kit, a micro-disease detection system, or an auto-navigation system. Also within the invention are methods for fabricating such apparatus.

100 Claims, 32 Drawing Sheets

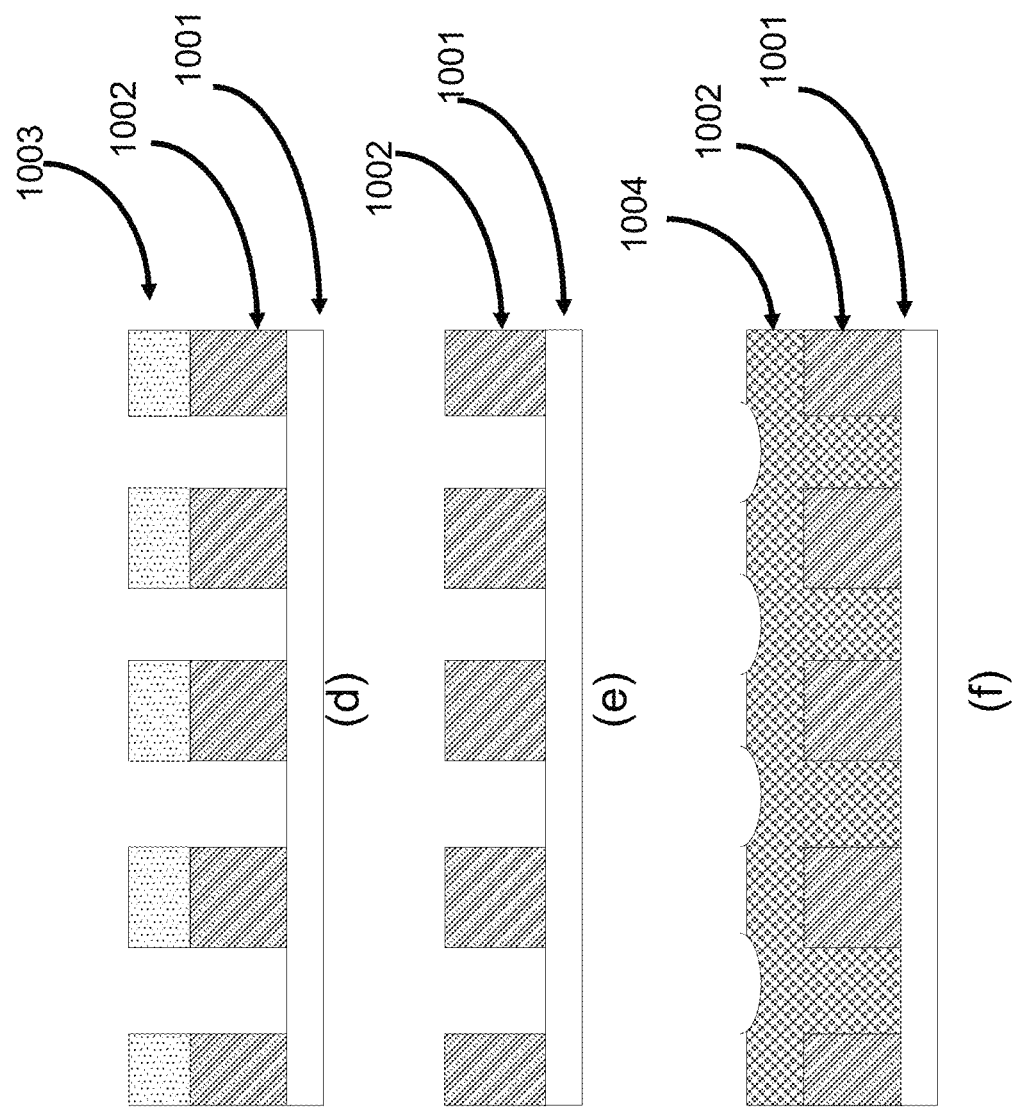

(n)

The insulating material 1002

(o)

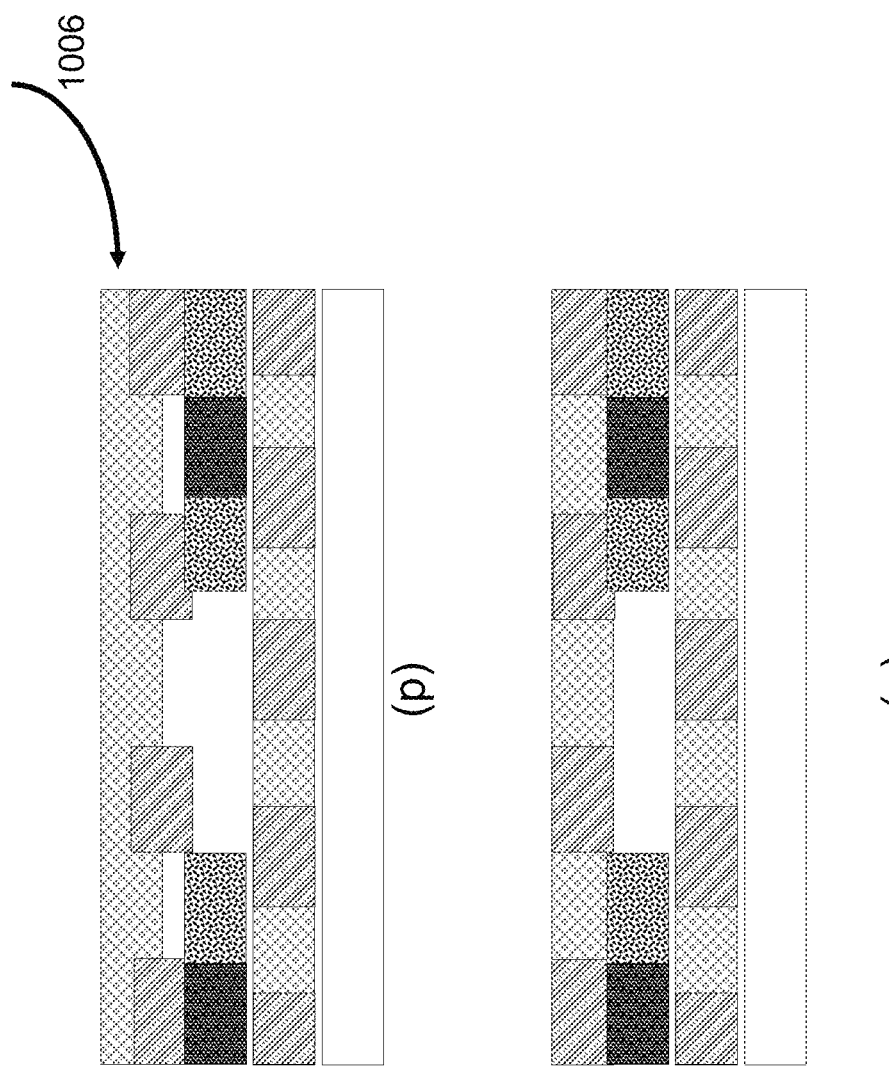

(v)

(j)

(k)

DECOMPOSABLE APPARATUS AND METHODS FOR FABRICATING SAME

BACKGROUND OF THE INVENTION

Many current and future medical applications involve or will involve utilization of various types of medical apparatus or devices inside body (in vivo). Such medical apparatus or devices include but are not limited to detection equipments for disease detection, drug carriers for delivering medicines, medical instruments for surgeries, and special devices for integrated treatments. It is often desirable for such medical apparatus or devices to disintegrate, decompose, or be dispelled after their use in vivo.

A common approach so far has been using a single biodegradable or biocompatible polymer (either natural occurring and then modified, or purely synthetic) as the basis for such apparatus or devices. Many of these biodegradable limit the types of original materials that one can use. Metal and inorganic materials are often not used in these apparatus or devices because of their chemical stability. As a result, where desired, inorganic or metal material's mechanical stability or strength has not been utilized.

On the other hand, sometimes, medical apparatus or devices for in vivo medical applications can be as large as several millimeters in size (or several cubic millimeters in volume). It is most desirable for a relatively large apparatus to decompose to the molecular level. However, many materials cannot be disintegrated to molecular level (e.g., a few angstroms in size) in vivo. It is very difficult for all materials used in an advanced, fully functional medical apparatus with optimum performance to completely decompose into the molecular level, even though some materials may be decompose to small molecular level. While some materials disintegrate in certain fluids inside the body when they are used separately, but they cannot be disintegrated when being used as part of a medical apparatus. Further, it is not easy to dispel a medical apparatus even if it is in miniaturized size. Therefore, as the need for microscopic operations and associated miniaturized medical apparatus and devices arise, how to remove or decompose such medical apparatus and devices has become increasingly important and presented a major challenge.

For instance, when detecting and/or curing diseases, under specific circumstances, medical apparatus and devices need to be disintegrated and decompose in vivo in human beings to continue the treatment. Traditional medical therapies use medicine which is expected to provide a relatively long-term, controllable and proportional dose releasing function to treat the diseases. Some therapies use decomposing materials when fabricating a medical device for in vivo treatment. However, there are limited options of materials that are capable of decomposing. Some materials, for example, glasses or ceramics, cannot be used during fabrication due to the fact that they are not decomposable materials.

There are some newly developed therapies aiming at achieving the same purpose. Targeted therapy treats diseases by interfering with specific targeted molecules needed for cancer or tumor growth. Micro-surgical robot is capable of being injected into human bodies and treating diseases at the targeted area.

Detection apparatus may also be needed to be placed into the human body for carrying out various detection tests.

However, both traditional and newly developed detection approaches and therapies face the difficulties in disintegrating after using various types of medical apparatus in vivo, or difficulties in removing the side products of the therapies, i.e., medicine carrier or micro robot, and difficulties in controlling the release of the medicine in a timely manner. Sometimes, it is difficult to remove a medical apparatus such as a miniaturized detection apparatus out of a human body. These drawbacks call for novel decomposing apparatus which not only overcomes existing issues, but also bring enhanced accuracy, safety, and specificity in medical detection, drug release, and surgeries.

SUMMARY OF THE INVENTION

The present invention in general relates to a class of innovative decomposable apparatus which utilizes building blocks and/or sub-components integrated with decomposable materials using the state-of-the-art micro-electronics technologies and processes.

In one aspect, this invention provides medical devices, micro-devices, medical instruments, or drug carriers (together "apparatus") that comprise building blocks at least one of which comprises a material that can decompose and result in disintegration of the building blocks (or the apparatus) into much smaller pieces or molecules (for example, as small as 0.1 micron in size). Because the surface area is increased greatly, the disintegrated micro or nano particles exhibits quite different chemical or physical properties with respect to the same macro object, and they are much more chemically reactive and prone to be degradable. For example, a building block of a size of 100 microns×100 microns can decompose into smaller pieces of 0.1 micron× 0.1 micron. The decomposition of the building blocks (or disintegration of the apparatus) can be triggered or activated, e.g., by being in contact with a solution, gas, or solid of a particular property (e.g., acidity or presume or ion strength), by an external signal (e.g., a chemical, mechanical, physical, or magnetic signal), by an agent or an energy stored in the apparatus, or by a chemical reaction with a surrounding substance (e.g., blood or stomach acid). With this disclosed, innovative approach, many innovative, miniaturized medical apparatus can be more effectively and broadly utilized in existing and future in vivo medical applications, enabling more design options, treatment capabilities, and more materials for such in vivo medical applications.

The apparatus of this invention and those fabricated by the methods of this invention may have a wide range of designs, structures, functionalities, and features. Specific examples of the above described apparatus with decomposition and disintegration features include, but are not limited to, voltage comparators, four-point probes, calculators, logic circuitries, memory units, micro-cutters, micro-hammers, micro-shields, micro-dyes, micro-pins, micro-knives, micro-needles, micro-thread holders, micro-tweezers, micro-optical absorbers, micro-mirrors, micro-wheelers, micro-filters, micro-choppers, micro-shredders, micro-pumps, micro-absorbers, micro-signal detectors, micro-drillers, micro-suckers, micro-testers, micro-containers, micro-injectors, signal transmitters, signal generators, friction sensors, electrical charge sensors, temperature sensors, hardness detectors, acoustic wave generators, optical wave generators, micro-heaters, heat generators, micro-refrigerators, and charge generators. In addition to the methods of this invention, these apparatus can also be fabricated by other methods as known in the art or described elsewhere, e.g., in PCT/US2010/049298, PCT/US2011/024672, U.S. Ser. No. 12/416,280, PCT/US2011/042637, and PCT/US2010/041001, the contents of all of which are incorporated herein by reference in their entireties.

In some embodiments of these medical apparatus, at least one of the buildings comprises a non-decomposable material. Examples of such material include non-degradable polymer which comprises polytetrafluoroethylene (PTFE), polyvinylchloride (PVC), polyamides (PA, Nylons), polyethylenes (PE), polysulfones, polyethersulphone, polypropylenes (PP), silicon rubbers, polystyrenes, polycarbonates, polyesters, polyacrylonitrile (PAN), polyimides, polyetheretherketone (PEEK), polymethylmethacrylate (PMMA), polyvinylacetate (PVAc), polyphenylene oxide, cellulose and its derivatives, polypropylene oxide (PPO), polyvinylidene fluoride (PVDF), polybutylene, and mixtures thereof, metal or metallic compounds (e.g., compounds or alloys containing calcium or magnesium or aluminum, copper, tungsten, silver), non-degradable inorganic salts or compounds (e.g., silicon, oxide, silicon, phosphate compounds or salts, silicon nitride, silicon carbide, silicon oxynitride, oxides), ceramics (e.g., a calcium phosphate ceramic), glass, an organic material, a biological material, or a composite thereof. Although these materials are not decomposable, Applicants nevertheless surprisingly found out that their inclusion into the medical apparatus of this invention enhances these apparatus' mechanical stability or strength and thus has made them suitable for applications where the current medical apparatus that are completely made of degradable materials are not suitable. In fact, it is believed that the present invention introduces for the very first time of such non-decomposable material into medical apparatus that are expected to decompose in vivo. Further, use of such materials has greatly increased the choices of materials used for manufacturing the decomposable and disintegrating medical apparatus which, for in vivo medical applications, have generally been made of degradable or decomposable materials entirely (and thus may not have completely satisfactory physical properties such as mechanical stability or strength).

Some embodiments of this invention include medical apparatus fabricated with building blocks of at least two materials with at least one of them decomposable, where decomposition of one material will result in disintegration of the building block, thereby enabling such apparatus capable of decomposing into smaller pieces or molecular levels.

In some embodiments, the invention provides decomposing apparatus, each comprising a first sub-component and a first micro device comprising a decomposable material, wherein the sub-component comprises a drug, a medical kit, a micro-disease detection system, or an auto-navigation system.

In some embodiments, the decomposable material comprises poly(lactide-co-glycolide) (PLGA), poly(lactide) (PLA), poly(L-lactic acid) (PLLA), poly(D,L-lactic acid) (PDLLA), polyglycolic acid (PGA), polyanhydrides, poly(ortho ethers), polyamino acids, engineered artificial proteins, natural proteins, biopolymers, polyvinyl alcohol, polyethylene oxide, polymethacrylic acid (PMAA), polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof. In some other embodiments, the decomposable material comprises poly(lactide-co-glycolide), poly(lactide), poly(L-lactic acid), poly(D,L-lactic acid), polyglycolic acid, polyanhydrides, poly(ortho ethers), polyamino acids, engineered artificial proteins, natural proteins, biopolymers, polyvinyl alcohol, polyethylene oxide, polymethacrylic acid, polyacrylic acid, polyethylene glycol, alginate, collagen, gelatin, hyaluronic acid, an organic material, a biological material, or a composite thereof.

In some embodiments, the decomposable materials are combinations of decomposable materials and other micronized materials that are not capable of decomposing. The other materials (e.g., glasses or ceramics) are fabricated into micro-sizes. In such combined materials, the decomposition of the decomposable material resulted in the disintegration of the combined material, mobilizing the micronized materials. The micronized materials with such sizes, even though not capable of degradation, can harmlessly exit human bodies through the waste system once they serve their purpose.

In some embodiments, the decomposable material can be activated to decompose by an external signal. The signal can comprise an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal.

In some embodiments, the electronic property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments, the decomposable material decomposes in a desired period of time. For instance, the desired period of time can range from one second to a couple weeks (e.g., from 5 seconds to 10 days, from 30 seconds to 1 week, from 2 minutes to 4 days, from 5 minutes to 3 days, from an hour to 3 days).

In some embodiments, the de-composition of a decomposable material occurs when it contact with a desired substance, e.g., a fluid such as blood or bile acid or a low-pH body fluid, a gas such as a triggering gas, or a solid with sufficient acidicity. Such substance is usually quite effective in inducing the chemical decomposition of the decomposable material.

In some embodiments, the first sub-component is integrated inside the first micro device; or the first sub-component is attached onto the surface of the first micro device.

In some embodiments, the first sub-component comprises a drug.

In some embodiments, the decomposable material can decompose in the in vivo environment of a human being.

In some embodiments, the apparatus each further comprises at least one more micro device comprising a decomposable material. In some of such embodiments, the sub-component can be positioned (e.g., sandwiched) in between two micro devices.

In another aspect, the invention provides nano-drug delivery apparatus, each comprising a nano-drug and a micro device comprising a decomposable material.

In some embodiments, the decomposable material comprises poly(lactide-co-glycolide), poly(lactide), poly(L-lactic acid), poly(D,L-lactic acid), polyglycolic acid, polyanhydrides, poly(ortho ethers), polyamino acids, engineered artificial proteins, natural proteins, biopolymers, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof.

In some embodiments, the decomposable materials are combinations of decomposable materials and other micronized materials that are not capable of decomposing. The other materials, for example, glasses, or ceramics are fabricated into micro-sizes. The materials with such sizes, even though are not capable of degradation, can be removed from the human bodies easily.

In some embodiments, the decomposable material is activated to decompose when an external signal is applied to it. The signal can comprise an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal.

In some embodiments, the electronic property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments, the decomposing material decomposes in a desired or pre-determined period of time which can range, e.g., from one seconds to a few weeks (e.g., from 1 seconds to 2 weeks, from 5 seconds to 1 week; from 1 minute to 4 days; from 20 minutes to 1 week, or from 3 hours to 10 days).

In some embodiments, the nano-drug is integrated into the micro device.

In some embodiments, the apparatus each further comprises at least one more nano-drug.

In some embodiments, the apparatus each further comprises at least one more micro device comprising a decomposable material.

In some embodiments, at least two nano-drugs are integrated in at least two different micro devices.

In some embodiments, the apparatus each further comprises a medical kit, a micro-disease detection system, or an auto-navigation system.

For instance, the micro-disease detection system detects a disease, and sends an external signal to the decomposable material to trigger the decomposition. The signal may comprise an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal.

In some embodiments, the electronic property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments, the auto-navigating system navigates the apparatus to a lesion and the apparatus performs a treatment at the lesion.

In yet another aspect, the invention provides apparatus for carrying drugs, each apparatus comprising a first drug, an inner micro device comprising a first decomposable material packaging the first drug, a second drug, and an outer micro device comprising a second decomposable material packaging the second drug, wherein the first drug is inside the inner micro device, and the second drug is positioned between the inner micro device and the outer micro device.

In some embodiments, the first drug and the second drug are the same.

In some embodiments, the first or second decomposable material comprises poly(lactide-co-glycolide), poly(lactide), poly(L-lactic acid), poly(D,L-lactic acid), polyglycolic acid, polyanhydrides, poly(ortho ethers), polyamino acids, engineered artificial proteins, natural proteins, biopolymers, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof. In some embodiments, the decomposable materials are combinations of decomposable materials and other micronized materials that are not capable of decomposing. The other materials, for example, glasses, or ceramics are fabricated into micro-sizes. The materials with such sizes, even though are not capable of degradation, can be removed from the human bodies easily.

In some embodiments, the decomposable material in the outer micro device or the inner micro device is activated to decompose when an external signal is applied to it. The signal may comprise an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal.

For instance, the electronic property can be surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property can be temperature or vibrational frequency; the optical property can be optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments, the decomposable material decompose in a desired period of time, e.g., from a couple seconds to a couple weeks.

In some embodiments, the materials in the outer and inner micro devices decompose at a same time or different times.

In some embodiments, the apparatus each further comprises a medical kit, a micro-disease detection system, or an auto-navigation system, which is integrated in the inner micro device or the outer micro device. The micro-disease detection system detects a disease and sends an external signal to the inner or outer micro device. The signal comprises an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal. For instance, the electronic property can be surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiment of the apparatus, the material in the inner or outer micro device is activated to decompose when the micro device receives the signal from the micro-disease detection system.

In some other embodiments of this invention, the auto-navigating system navigates the apparatus to a lesion and the apparatus performs a treatment in the lesion.

Another aspect of this invention relates to methods for fabricating a decomposable apparatus. Each method includes the following steps: providing a substrate; optionally depositing a liner material; depositing a first material onto the substrate, wherein the first material is decomposable; patterning the first material to create recessed areas in the layer of the first material; depositing a second material onto the first material and the substrate, wherein the second material is different from the first material; planarizing or etch back the second material to stop on the layer of the first material; optionally repeating the above processes of forming a layer with at least two materials with at least one material decomposable to form multiple components; and removing the substrate.

Still another aspect of this invention relates to methods for fabricating a decomposable apparatus. Each method includes the following steps: providing a substrate; optionally depositing a liner material; depositing a first material onto the substrate, wherein the first material is decomposable; depositing a photoresist onto the first material; subjecting the photoresist to a UV light, visible light, an electromagnetic wave, electron, or an ion beam and developing the photoresist to a desired shape; etching the first material using the remaining photoresist as a mask, to form a desired shape, and removing the remaining photoresist; depositing a second material onto the first material and the substrate, wherein the second material is different from the first material; planarizing or etch back the second material to stop on the layer of the first material; repeating the above processes to form additional layer or structures comprising of at least two materials with at least one of them decomposable; and removing the substrate.

In some embodiments, the substrate comprises silicon, oxide, polysilicon, sapphire, a phosphate compound, a zirconium compound, or a calcium compound.

In some embodiments, the photoresist comprises methacryl, acryl, α-(trifluoromethyl)-acryl, norbornene, vinyl, or styrene monomers with fluoroalcohol.

In some embodiments, the first material comprises of silicon nitride, silicon carbide, silicon oxynitride, aluminum oxide, a metal (aluminum alloy, copper, copper alloy, and tungsten), and a semiconductor.

In some embodiments, the light with a desired wave length is visible or invisible.

In some embodiments, the second material is also decomposable.

In some embodiments, the first decomposable material comprises poly(lactide-co-glycolide), poly(lactide), poly(L-lactic acid), poly(D,L-lactic acid), polyglycolic acid, polyanhydrides, poly(ortho ethers), polyamino acids, engineered artificial proteins, natural proteins, biopolymers, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof.

In some embodiments, the decomposable materials are combinations of decomposable materials and other micronized materials that are not capable of decomposing. The other materials, for example, glasses, or ceramics are fabricated into micro-sizes. The materials with such sizes, even though are not capable of degradation, can be removed from the human bodies easily.

In some embodiments, the second decomposable material comprises poly(lactide-co-glycolide), poly(lactide), poly(L-lactic acid), poly(D,L-lactic acid), polyglycolic acid, polyanhydrides, poly(ortho ethers), polyamino acids, engineered artificial proteins, natural proteins, biopolymers, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof.

In some embodiments, the decomposable materials are combinations of decomposable materials and other micronized materials that are not capable of decomposing. The other materials, for example, glasses, or ceramics are fabricated into micro-sizes. The materials with such sizes, even though are not capable of degradation, can be removed from the human bodies easily.

In some embodiments, the decomposable material is activated to decompose when an external signal is applied to it. The signal can comprise, e.g., an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal.

In some embodiments, the electronic property is surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, oxygen concentration, oxygen consumption rate, ionic strength, catalytic behavior, or bonding strength; the physical property is density or geometric size; the acoustic property is frequency, speed of acoustic waves, acoustic frequency and intensity spectrum distribution, acoustic intensity, acoustical absorption, or acoustical resonance; and the mechanical property is internal pressure, hardness, shear strength, elongation strength, fracture stress, adhesion, mechanical resonance frequency, elasticity, plasticity, or compressibility.

In some embodiments, the decomposing material decomposes in a desired period of time, e.g., from a couple seconds to a couple weeks.

In some embodiments, the second material is planarized by chemical polishing, mechanical polishing, or chemical-mechanical polishing.

In some embodiments, etching comprises wet etching, dry etching, or vapor etching.

In some embodiments, the method further comprises repeating the steps of etching an existing material, depositing another material, and planarizing the further deposited material to result in a decomposable apparatus comprising at least two layers.

Still another aspect of this invention provides methods for fabricating a decomposable apparatus, each comprising the steps of: providing a substrate; optionally depositing a thin layer of material which can be removed later to separate the apparatus thus fabricated from the substrate; depositing a first material onto the substrate, wherein the first material is decomposable; patterning the first material with microelectronic technologies to form a recessed area in the first material; depositing a second material onto the first material and the substrate, wherein the second material is different from the first material; planarizing the second material to remove the second material from the top of the first material and stopping on the layer of the first material; optionally repeating the patterning, depositing, and planarizing steps set forth above with one or more additional materials to give rise to the apparatus, wherein each of the one or more additional materials is different from the material deposited right before this one additional material; optionally fabricating one or more additional components on the same substrate by repeating the depositing a new first material, patterning the new first material, depositing a new second material, or planarizing the new second material as describe above; and removing the optional thin layer from the substrate to separate the apparatus and optional additional components from the substrate.

Still another aspect of this invention provides methods for fabricating a decomposable apparatus, each comprising: providing a substrate; optionally depositing a thin layer of material which can be removed later to separate a material stack to be fabricated from the substrate; depositing a first material onto the substrate, wherein the first material is decomposable; patterning the first material with lithography and etch processes to form a recessed area in the first material; depositing a second material onto the first material and the substrate, wherein the second material is different from the first material; planarizing the second material from the top of the first material and stopping on the layer of the first material; optionally repeating the patterning, depositing, and planarizing steps set forth above with one or more additional materials to build additional features (e.g., one or more even more complicated structures or functional units, such as a circuit including transistor, wiring, and interconnects), thus giving rise to the decomposable apparatus, wherein each of the one or more additional materials is different from the material deposited right before this one additional material; optionally repeating the depositing, patterning, depositing, or planarizing to fabricate one or more additional components which may or may not be connected to the apparatus; and removing the optional thin layer to separate the apparatus and optional additional components from the substrate.

Microelectronics technologies as described in PCT/US2011/042637 can also be used for the fabricating methods described above.

As used herein, "a decomposable material" refers to a material that breaks down in vivo of a biological subject (e.g., a human being). It generally can be replaced with the term "a degradable material."

As used herein, a "component" or "sub-component" or "micro-device" typically refers to a device fabricated by microelectronics processes or technologies from one or more materials. Usually, the more complicated or functional a component or subcomponent is, the more types of materials will be used in fabricating them. Examples of the component or sub-component or micro device include, but are not limited to, comparators, four-point probes, calculators, logic circuitries, memory units, micro-cutters, micro-hammers, micro-shields, micro-dyes, micro-pins, micro-knives, micro-needles, micro-thread holders, micro-tweezers, micro-optical absorbers, micro-mirrors, micro-wheelers, micro-filters, micro-choppers, micro-shredders, micro-pumps, micro-absorbers, micro-signal detectors, micro-drillers, micro-suckers, micro-testers, micro-containers, micro-injectors, signal transmitters, signal generators, friction sensors, electrical charge sensors, temperature sensors, hardness detectors, acoustic wave generators, optical wave generators, micro-heaters, heat generators, micro-refrigerators, and charge generators.

As used herein, "photoresist" refers to a light-sensitive material used to form a patterned coating on a surface. For example, it can be used as a hard mask during etching processes.

As used herein, the term "drug" refers to a chemical or biological element that has therapeutic or pharmaceutical effect and is effective in reducing the severity of or eliminating a disease or disorder. Examples of the drug include, but are not limited to, both small molecule drugs and big molecular drugs such as proteins.

As used herein, the term "nano-drug" refers to a nano-sized or nano-scale chemical or biological element that has therapeutic or pharmaceutical effect and is effective in reducing the severity of or eliminating a disease or disorder.

As used herein, the term "medical kit" refers to a kit that can be used to perform a medical procedure including, but not limited to, medicine administration, surgery, disease detection, medical device implantation, and cleaning, in a biological subject.

As used herein, the term "apparatus" refers to an instrument which typically comprises of at least one component, and can be used to perform medical functions in a biological subject.

As used herein, the term "micro-device" refers to a device fabricated by microelectronics or semiconductor processes which typically has integrated, multiple components, and can be used to perform a wide range of tasks in a biological subject.

As used herein, the term "a micro-disease detection system" refers to a system that can detect disease based on a property at the microscopic level of a biological subject.

As used herein, the term "auto-navigation system" refers to a system that can automatically navigate itself, either with a demand pre-entered into it or with a demand that is communicated to it in situ.

As used herein, the term "interlaced structure" refers to a structure constructed by at least two basic types of geometrical units, with one type of unit surrounded by the other types of units (for example, one cube of unit type A is surrounded by six cubes of unit type B). Geometrically, the two types of basic units can be the same (for example, both are cubes of the same size and shape). But they may have different properties (for example, comprising different materials, different thermal expansion coefficients, different optical absorption properties, different melting points, etc.). One unique feature of this "interlaced structure" is that when one of the two types of basic units shrinks, melts, evaporates, or dissolves or otherwise change its geometric parameter (e.g., size or volume or shape), the whole structure is interrupted and decomposed into smaller pieces, with the largest size after the decomposition equal to the size of the largest basic unit, resulting in the disintegration of the structure. For example, if an interlaced cube structure of 1 mm×1 mm×1 mm in size is made of two types of basic cube units of 1 micron×1 micron×1 micron in size, after one of the basic type of cubes shrinks (in size), it will decompose into smaller pieces with size no larger than 1 micron×1 micron×1 micron.

As used herein, the term "decomposition" or "decompose," either by itself or as part of a combined word (e.g., "decomposable"), unless otherwise specified in more detail (for example, decomposed at the molecular level), refers to the partial or complete degradation or breakdown of the material into smaller piece or building blocks or components or molecules. Or, in other words, the term "decomposition" or "decompose" or "decomposable" as used herein, unless otherwise specified in more detail (e.g., decomposing at the molecular level), generally means that an original matter (e.g., an apparatus of a size on the order of 1 mm×1 mm×1 mm) is separated into smaller pieces (e.g., into pieces of 1/100 of its original linear size, 10 microns×10 microns×10 microns). Specifically, there are at least two levels of decomposition. At the first level, a material can be decomposed at or to the molecular level at a desired environment such as in a desired gas, a desired solution, a desired temperature, or a desired optical energy. As an example of the decomposition at the molecular level, a silicon dioxide material can be dissolved in a hydrofluoric acid (HF) solution, decomposing (dissolving) at the molecular level. Such decomposition to the molecular level does not require that the material decompose to the smallest molecule possible, rather, decomposition to a molecule of a lower molecular weight (or a shorter chain of a polymer molecule) would also suffice. At the second level, a material, e.g., a composite material or structure fabricated by the methods described herein, can be decomposed from its originally relatively large size (for example, millimeter in size) into a much smaller size (for example, 0.1 micron in size). One such example is a composite block of 1 micron (in thickness) by 500 microns (in width) by 1000 microns (in length) consisting of silicon dioxide and polysilicon in alternating cubes (1 micron×1 micron×1 micron in dimension) fabricated using the semiconductor processes disclosed in this application. When this composite block is submerged in an HF solution, with silicon dioxide dissolved in the solution, the 1 micron×500 micron×1000 micron composite block is decomposed into many 1 micron×1 micron×1 micron polysilicon pieces, which are much smaller than that of the original composite block. The advantages of this second approach (to which this invention particularly relates to) include: (1) many useful materials which cannot be used for in vivo medical applications due to their inability to decompose now can be utilized, (2) the composite materials can be stronger (for example, mechanically stronger), more stable (e.g., chemically), and more versatile than the currently used biological materials or biodegradable or biocompatible materials, and (3) with increased choices for materials, more functionality and higher performance for in vivo medical applications can be achieved with the composite materials using for the apparatus of this invention or for the fabrication methods disclosed herein.

For the decomposable apparatus of this invention, decomposition can be triggered by one method or a combination of the two or more methods which include but are not limited to: (a) decomposition in a desired environment which is often inside a biological system (i.e., in vivo) and which can a gas, a solid, a liquid such as a blood steam, a low pH fluid (e.g., a fluid in a human stomach), an urine, or a mucus) and in which the apparatus is placed or moved to, (b) an external signal which will in turn trigger an event to decompose the apparatus (for example, the signal can trigger the launch of an acoustic wave, a heat pulse, a laser team, or electrical pulse to decompose the apparatus), and (c) release of an agent such as a gas, fluid, or an energy which has been stored within the apparatus which is released at pre-programmed time, by remote control, or by an external signal.

The decomposable apparatus of this invention typically comprises blocks with (1) material(s) which can be decomposed at the molecular level; (2) at least two materials which form interlaced patterns, with at least one material which can be decomposed at molecular level; or (3) at least two materials which are fabricated to form interlaced patterns with at least one of them whose size can be reduced in a desired environment, by a triggering signal, or by a decomposing agent or decomposing means stored in the apparatus.

As used herein, the term "package" as in "packaging" refers to integrating (wherein the packaged element becomes part of the packaging material) or enclosing (wherein the packaged element is inside or encircled by the packaging material).

As used herein, a "biological material" refers a material that is naturally occurring and may or may not have been modified. Examples of such biological materials include protein, chitosan, rubber, or silicone polymer.

As used herein, an "organic material" refers to a material that is largely based on carbon and hydrogen, optionally with other elements such as halo or nitrogen or oxygen. It contrasts with inorganic materials.

As used herein, the term "photoresist" refers to a light-sensitive material used in several industrial processes, such as photolithography and photoengraving to form a patterned coating on a surface.

BRIEF DESCRIPTIONS OF THE FIGURES

Figure 8:
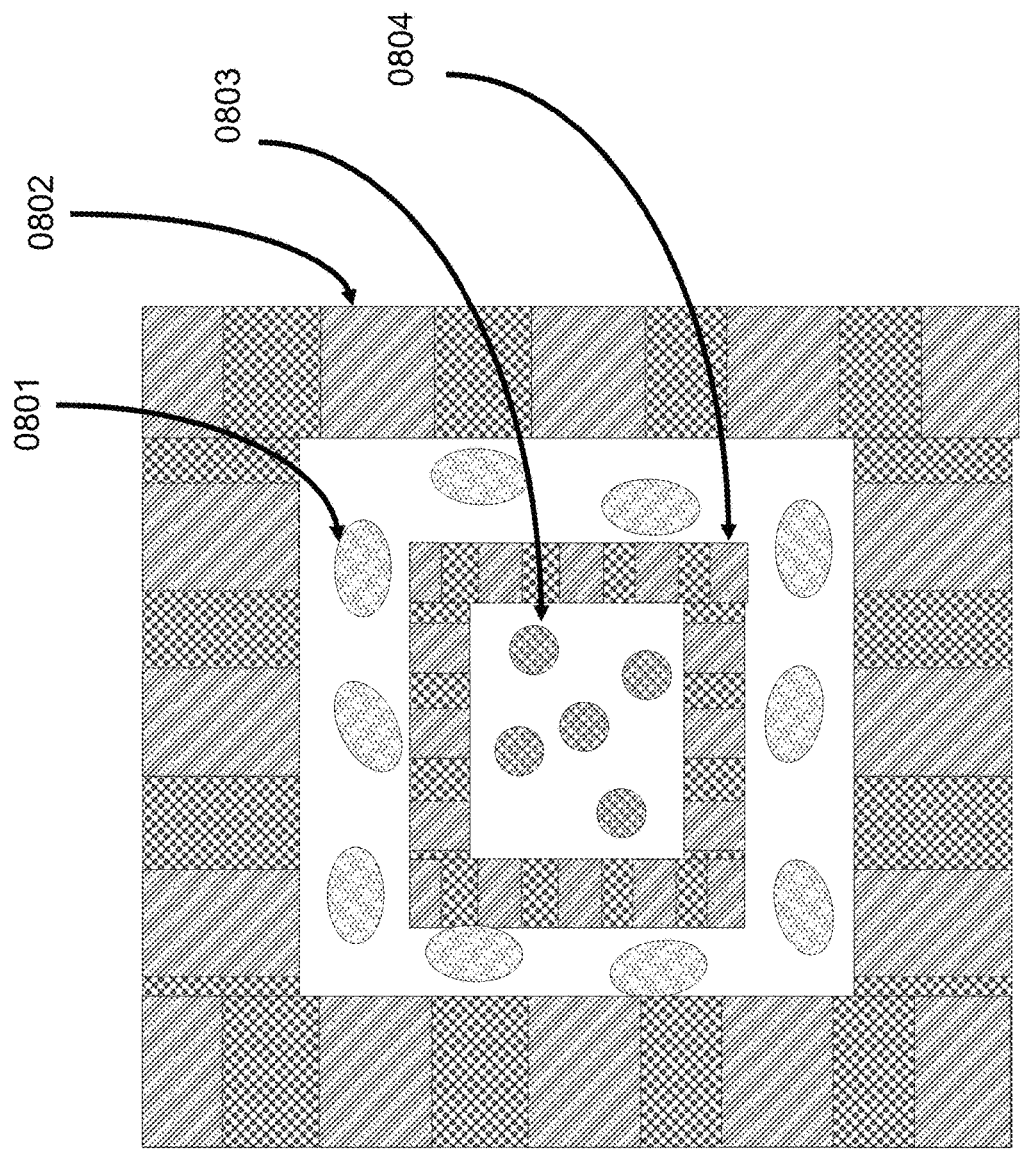
Figure 8:
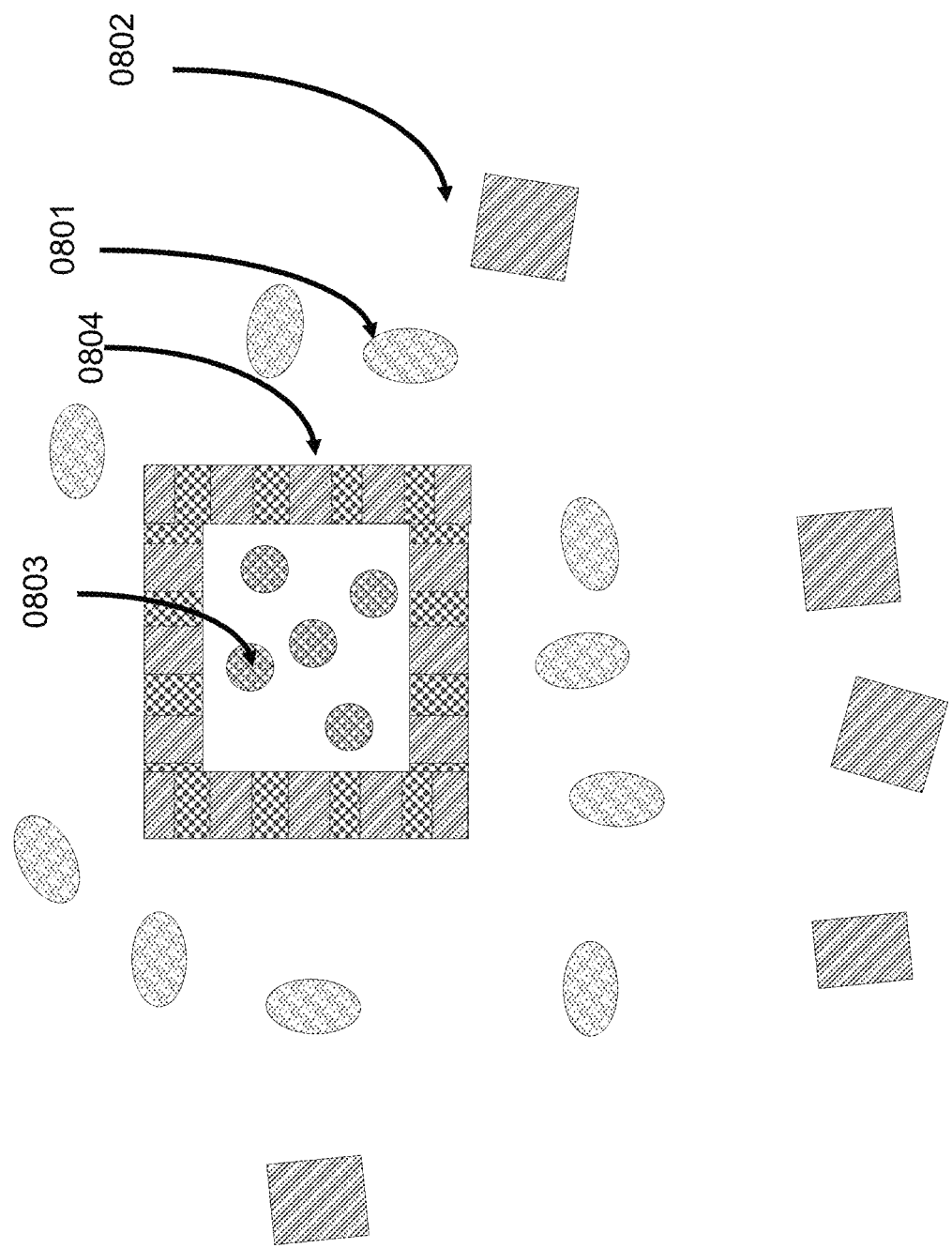
Figure 8:
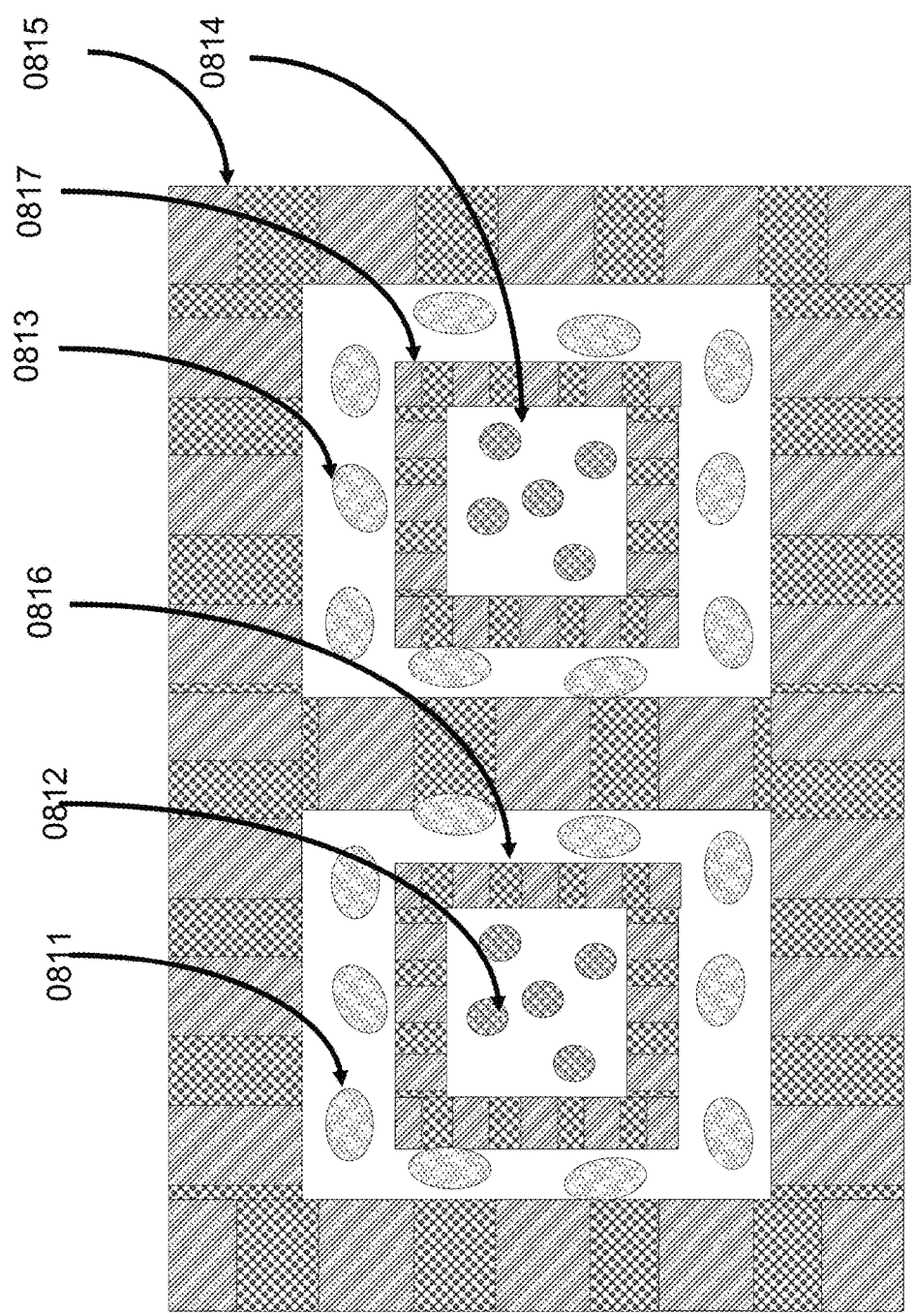

FIG. 8 shows an array of drug delivery apparatus with inner layers and outer layers of decomposable materials and at least two drugs. One of the drugs is packaged by the inner layer of decomposable material, while the second drug is sandwiched between the outer and inner layers of decomposable material. Such an arrangement enables the drugs being released at different times.

Figure 9:
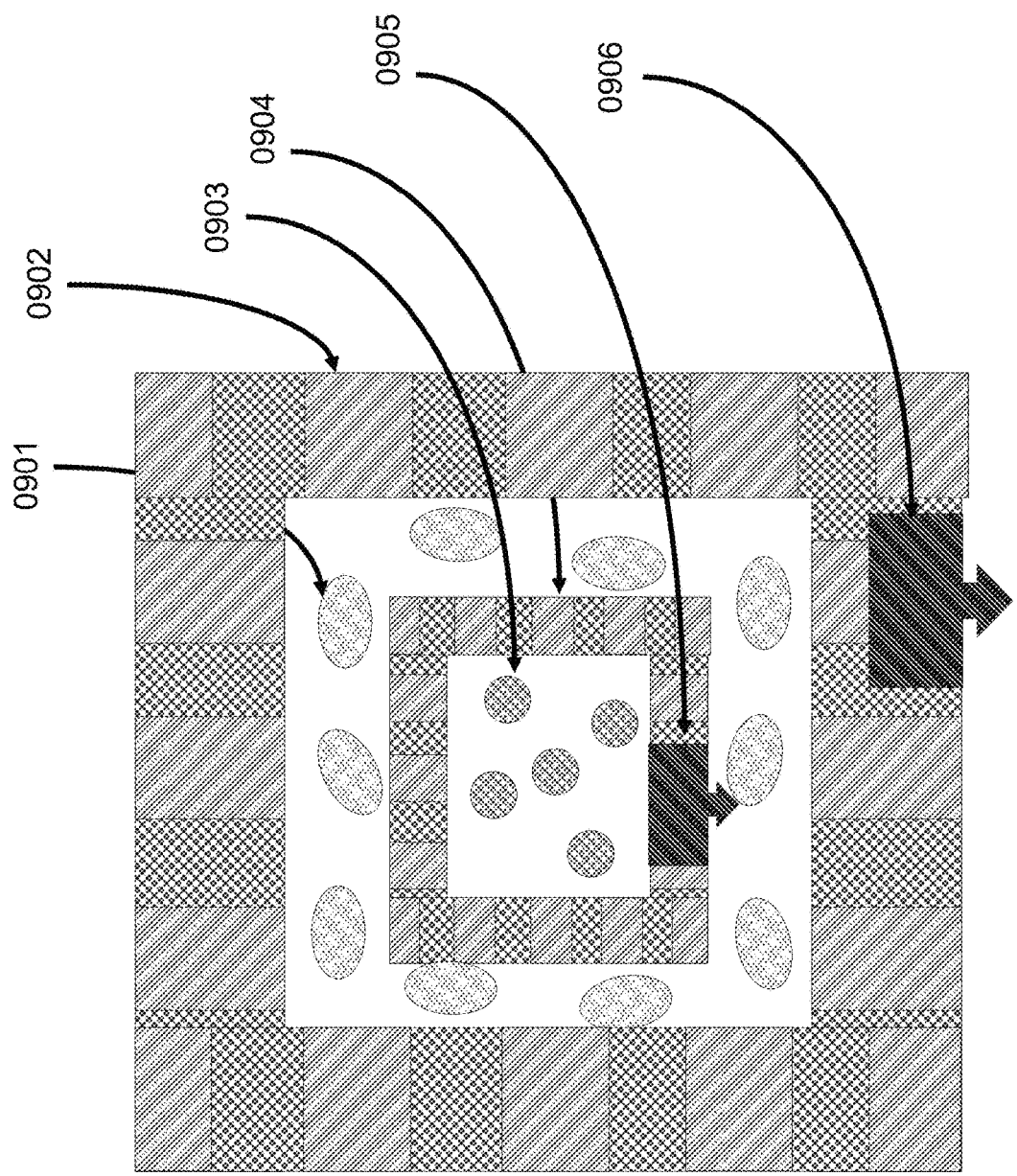
Figure 9:
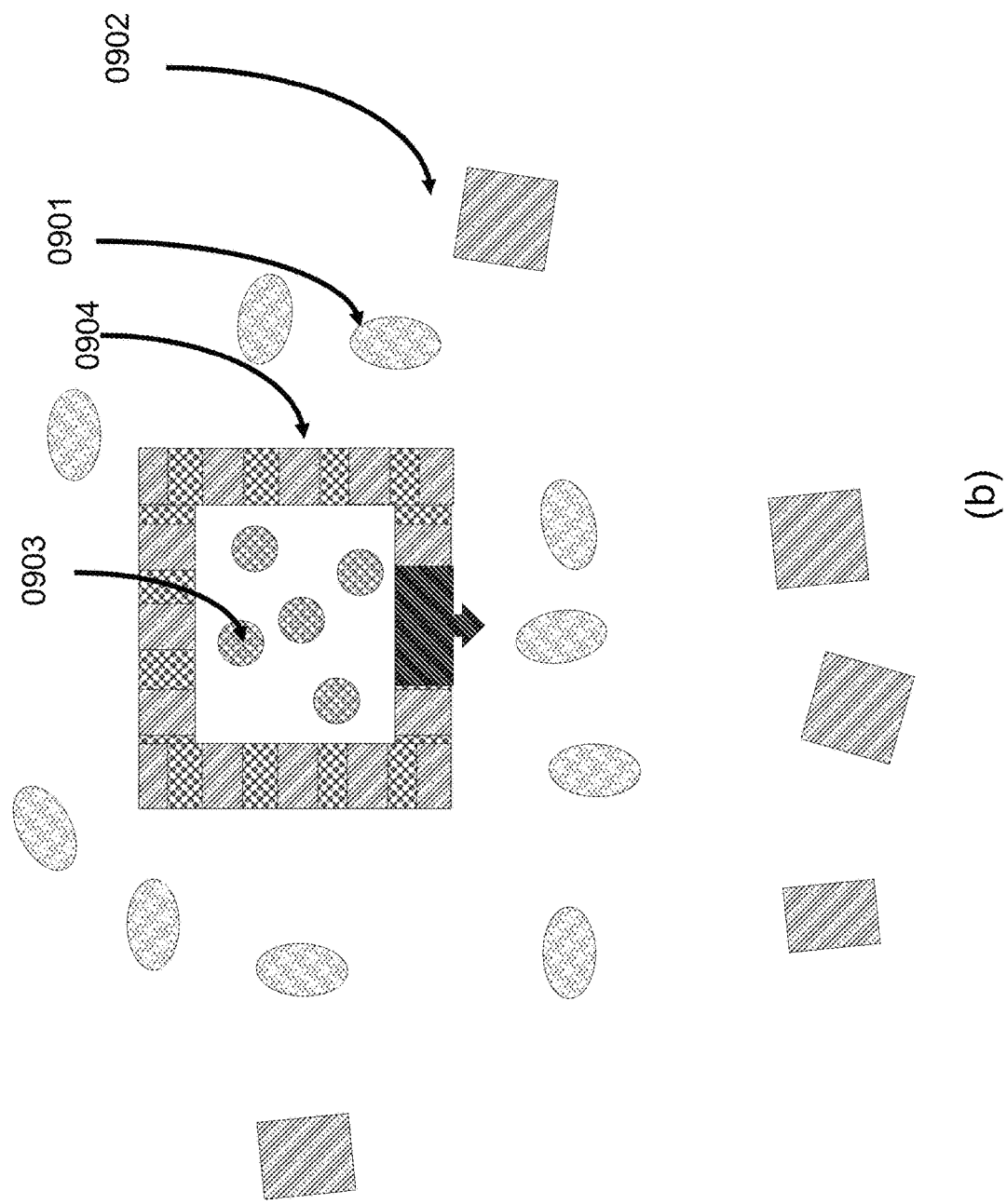

FIG. 9 illustrates an apparatus of this invention wherein micro-disease detection apparatus are integrated into the inner and outer layers of decomposable materials. The micro-disease detection apparatus sends an external signal to the decomposable material and activates the decomposition. Consequently, the drug that has been packaged by the layer is released. The two drugs are released at different times.

Figure 10:
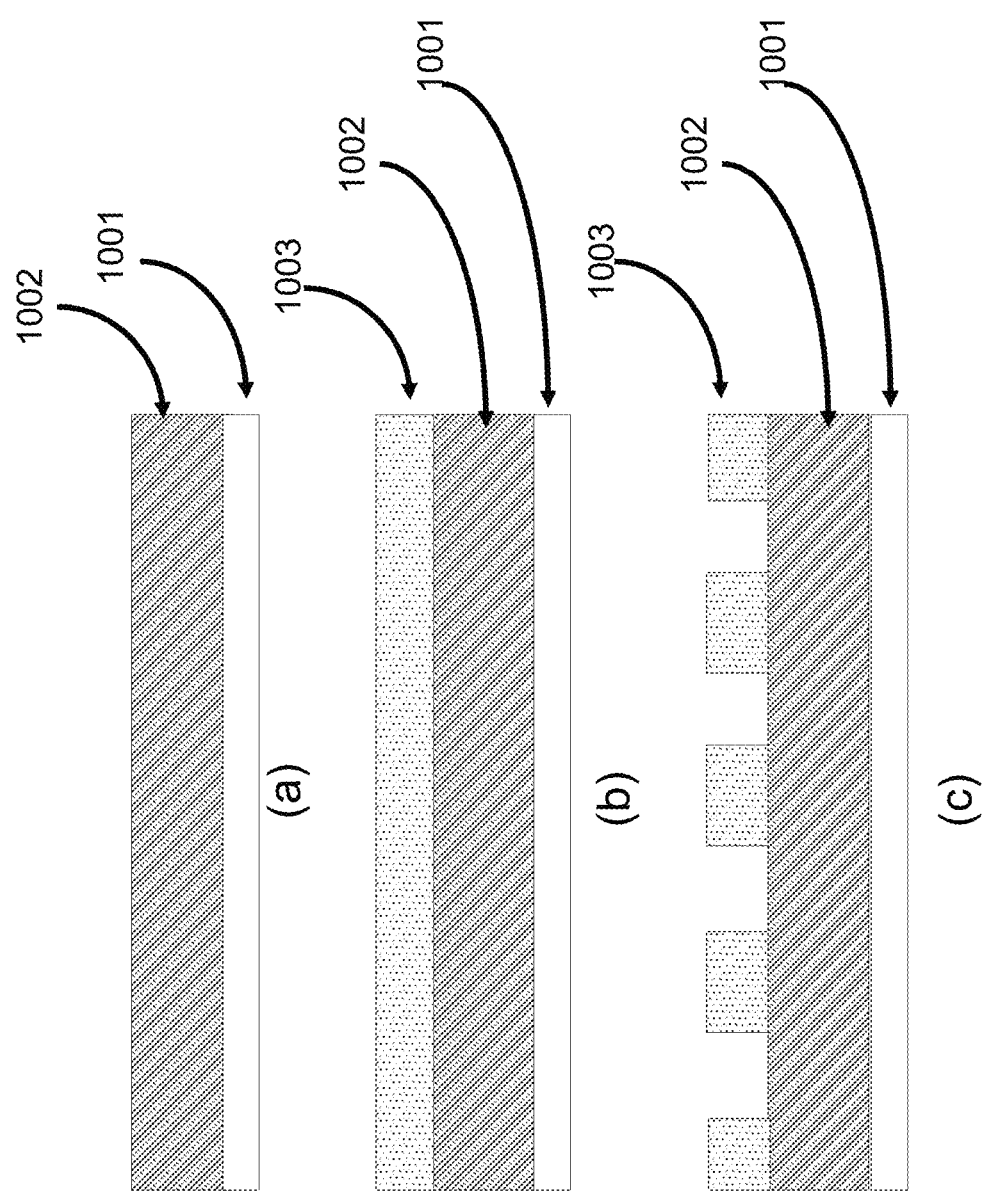
Figure 10:
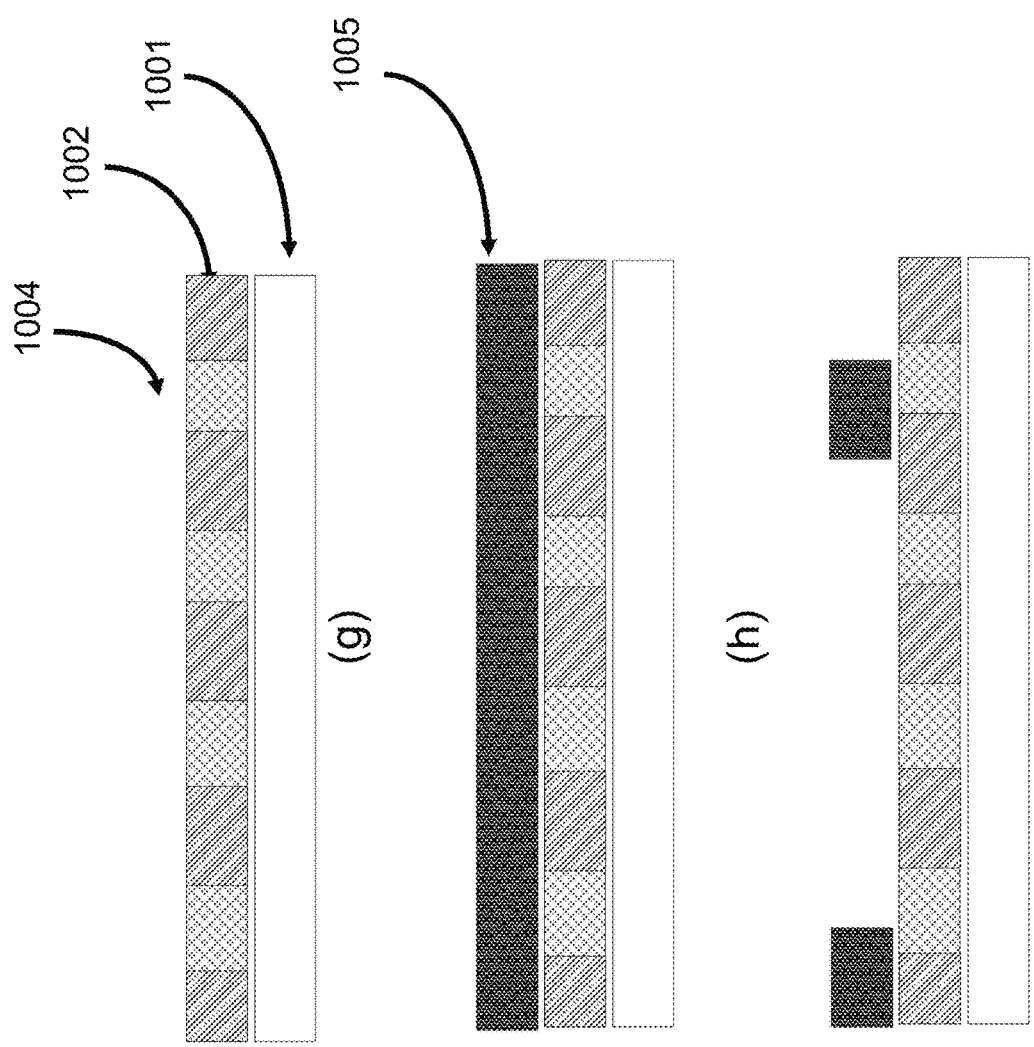
Figure 10:
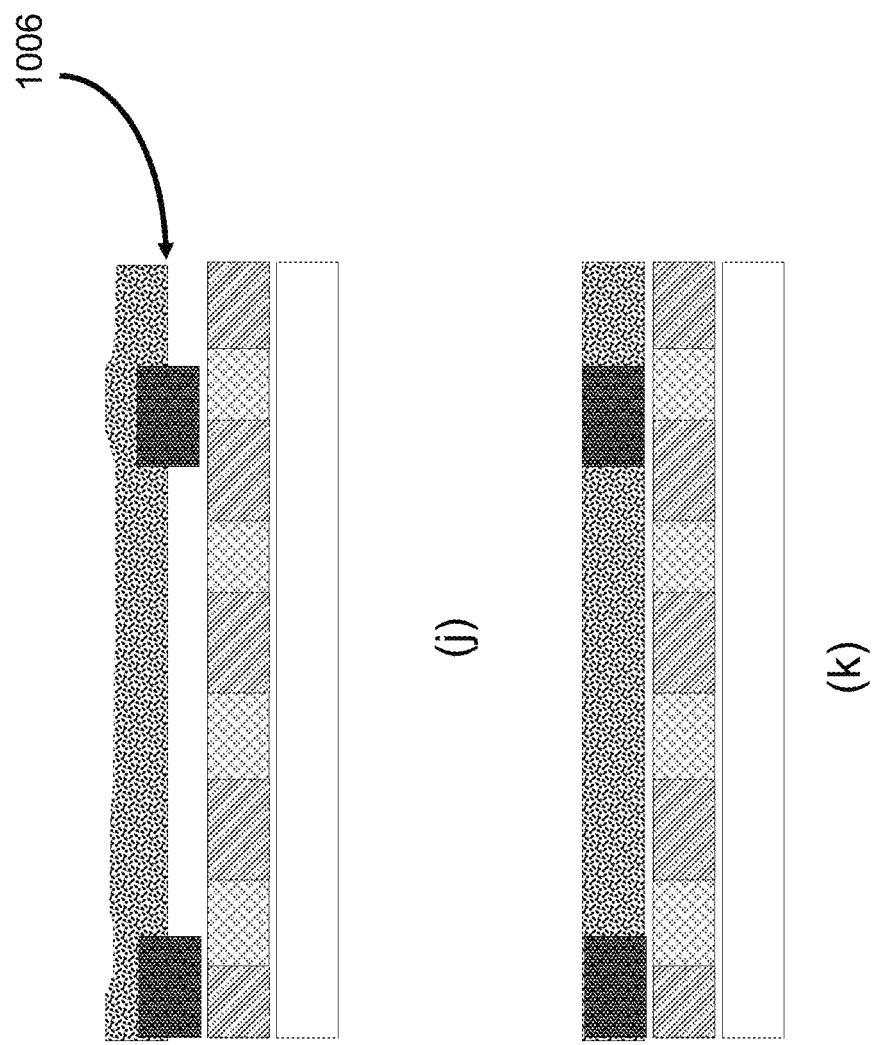
Figure 10:
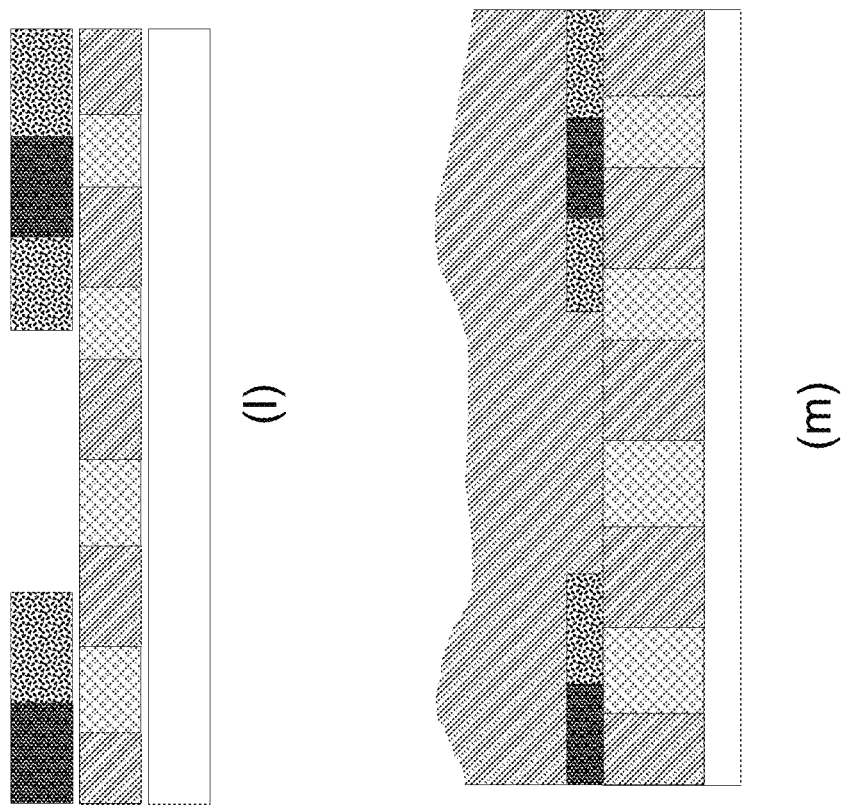
Figure 10:
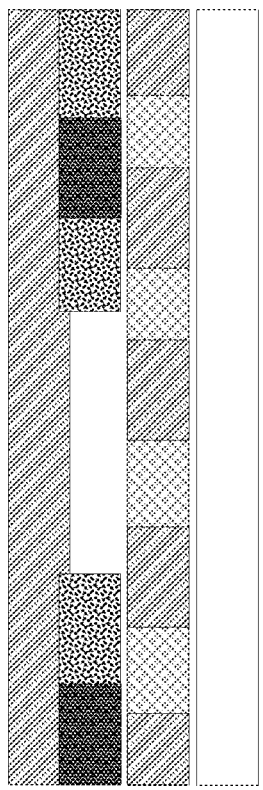
Figure 10:
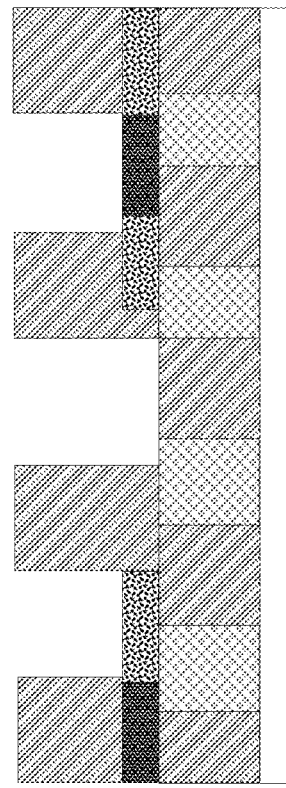
Figure 10:
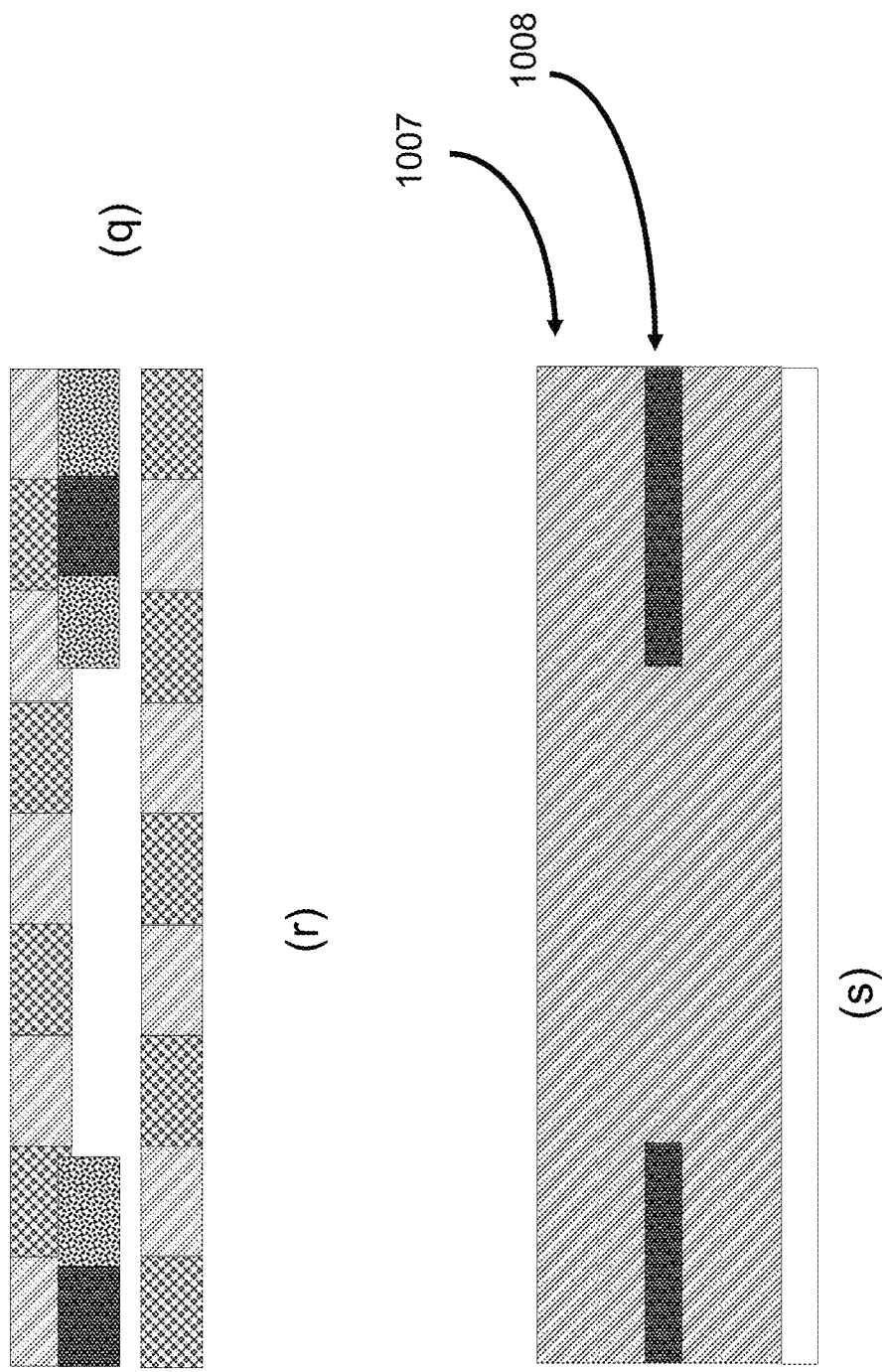
Figure 10:
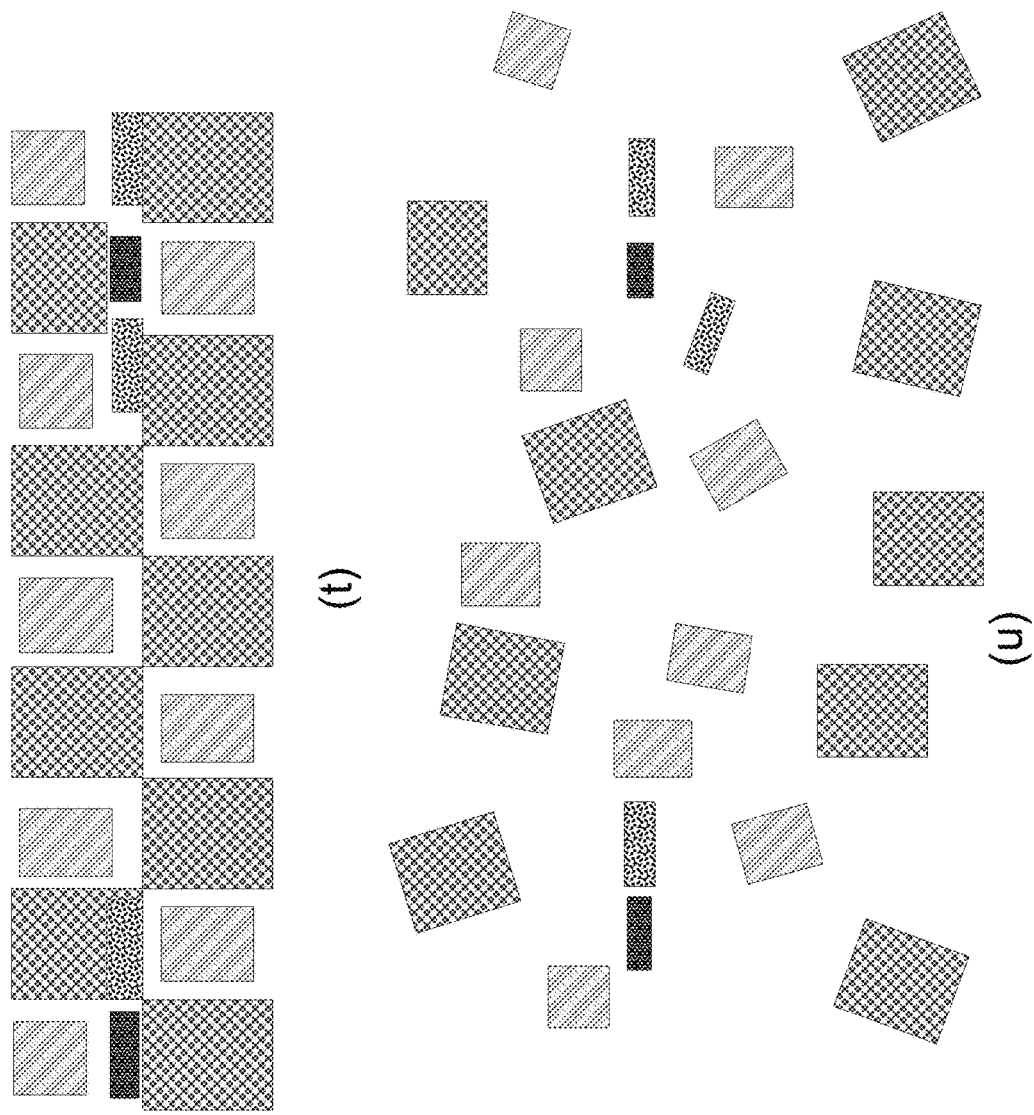
Figure 10:
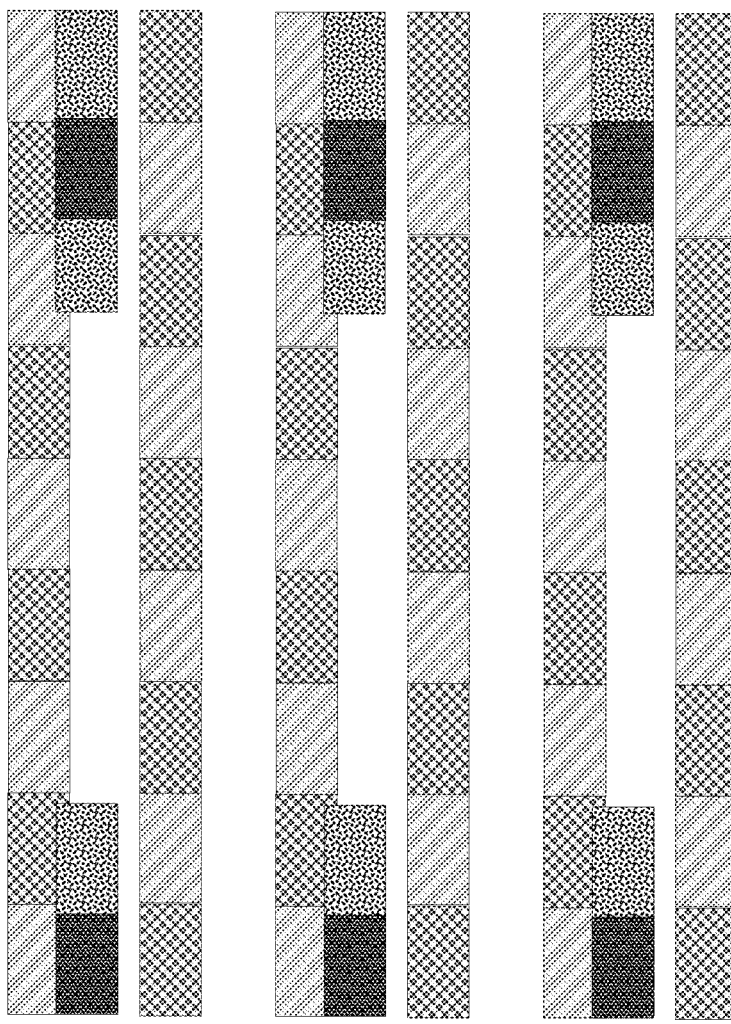

FIG. 10 illustrates a novel process flow for fabricating a decomposable apparatus of this invention by utilizing micro-electronics technologies and processes.

Figure 11:
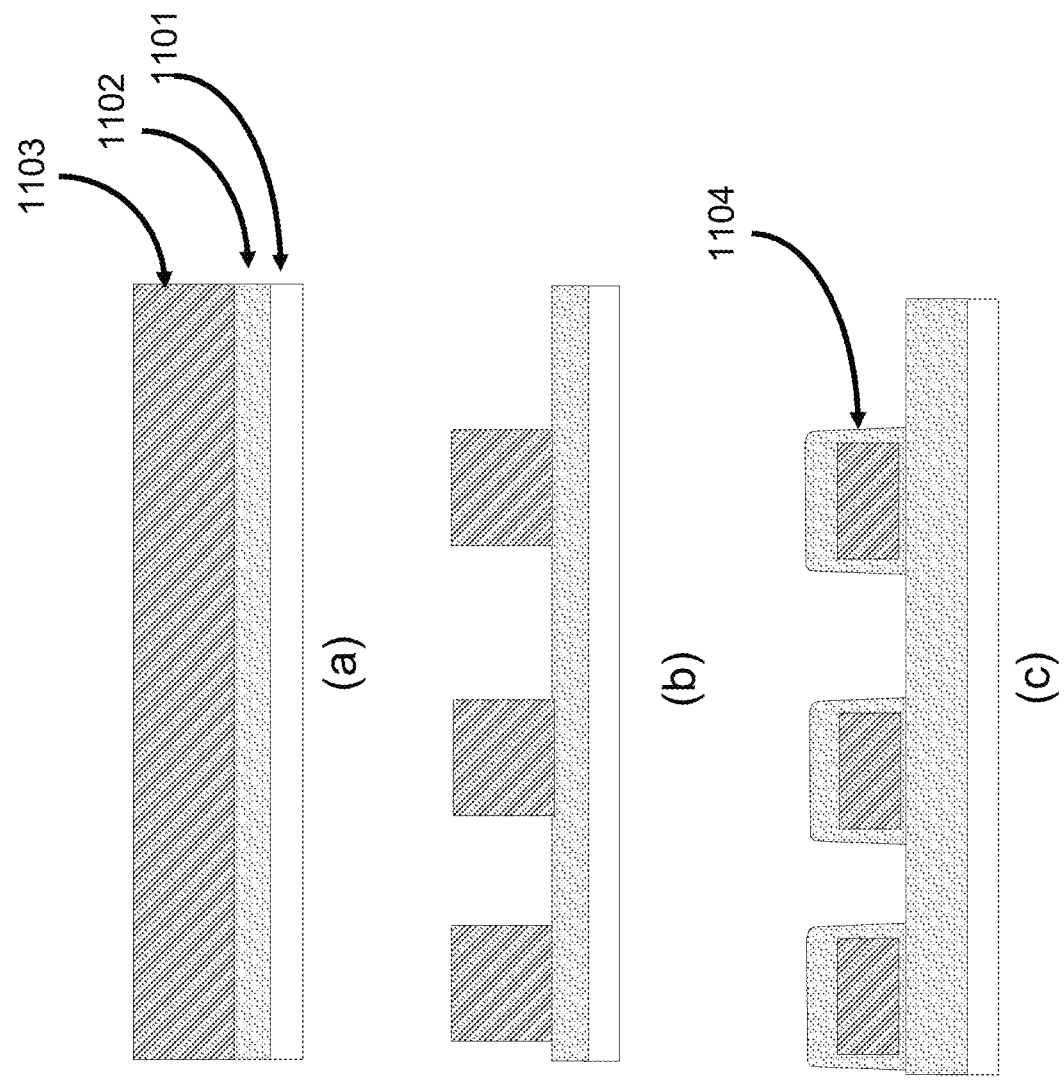
Figure 11:
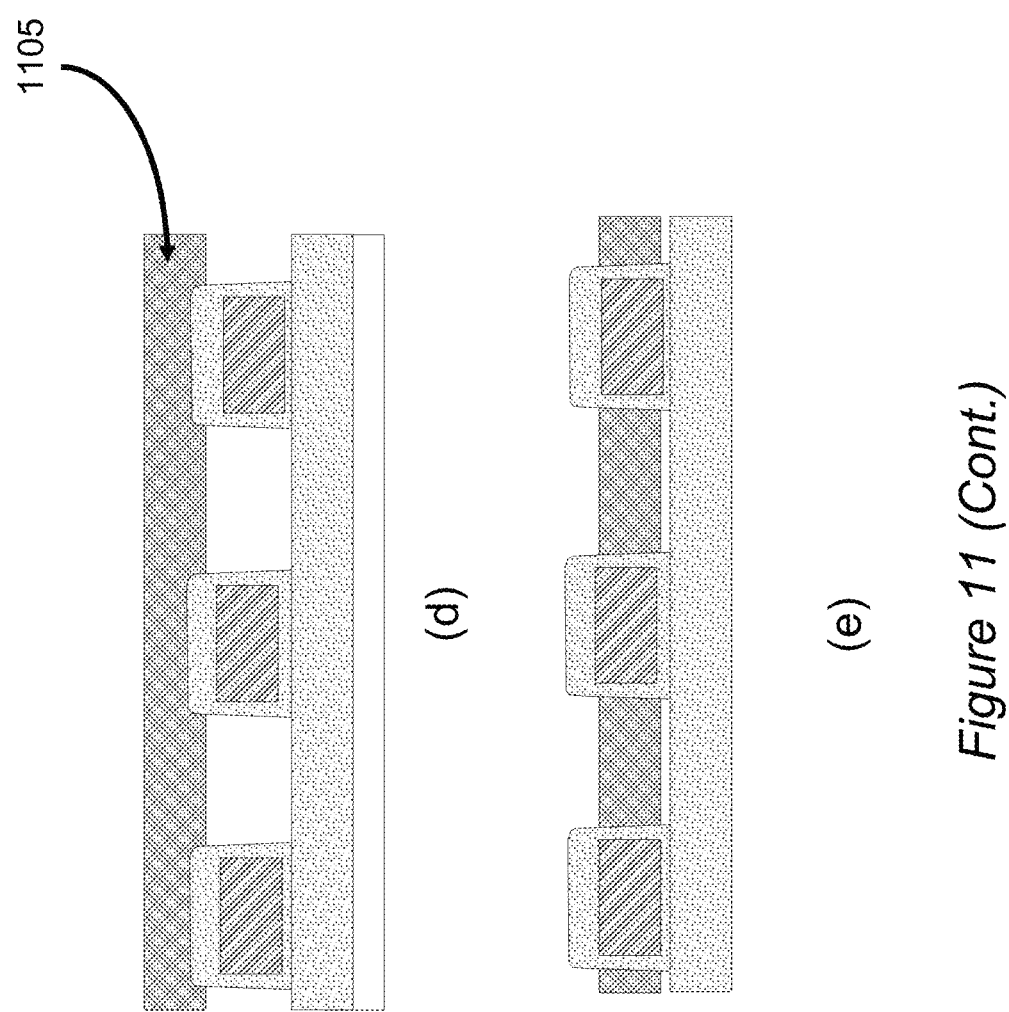
Figure 11:
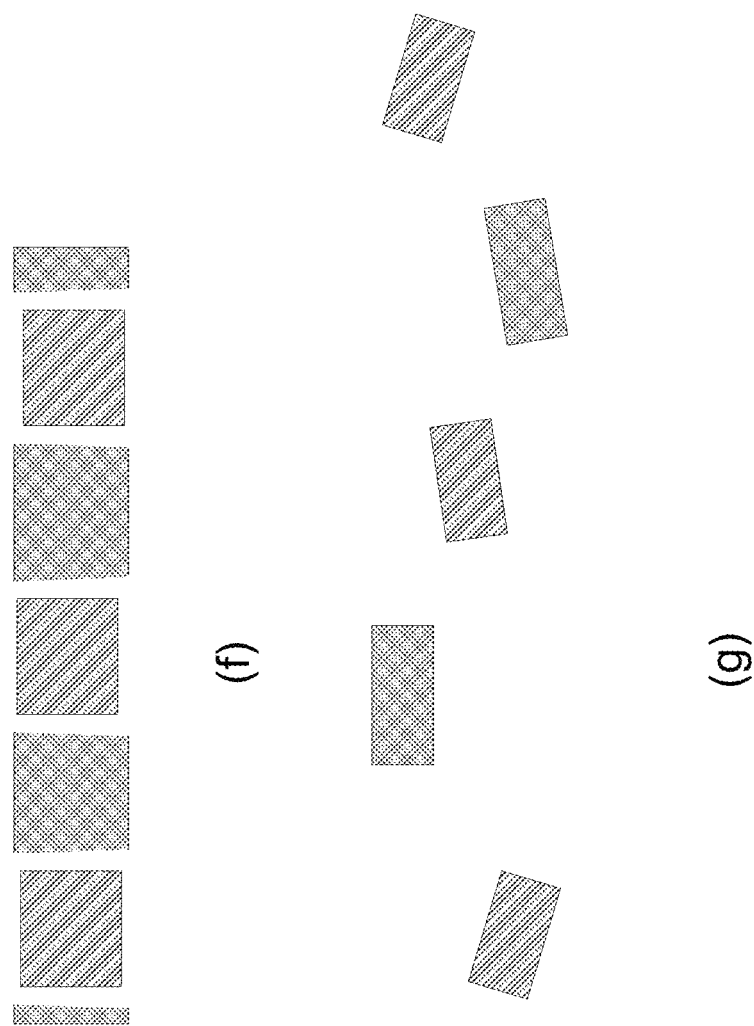

FIG. 11 illustrates another method for fabricating a decomposable apparatus of this invention.

Figure 12:
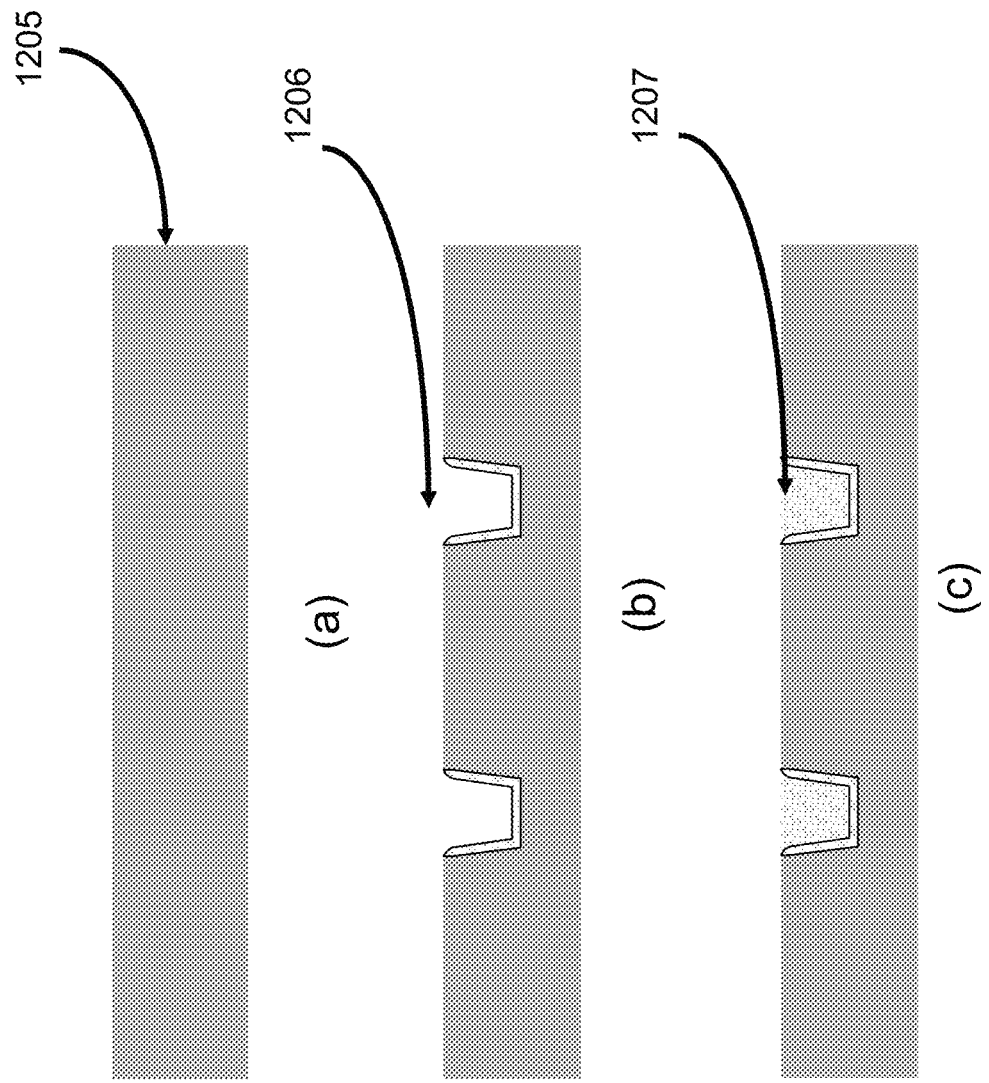
Figure 12:
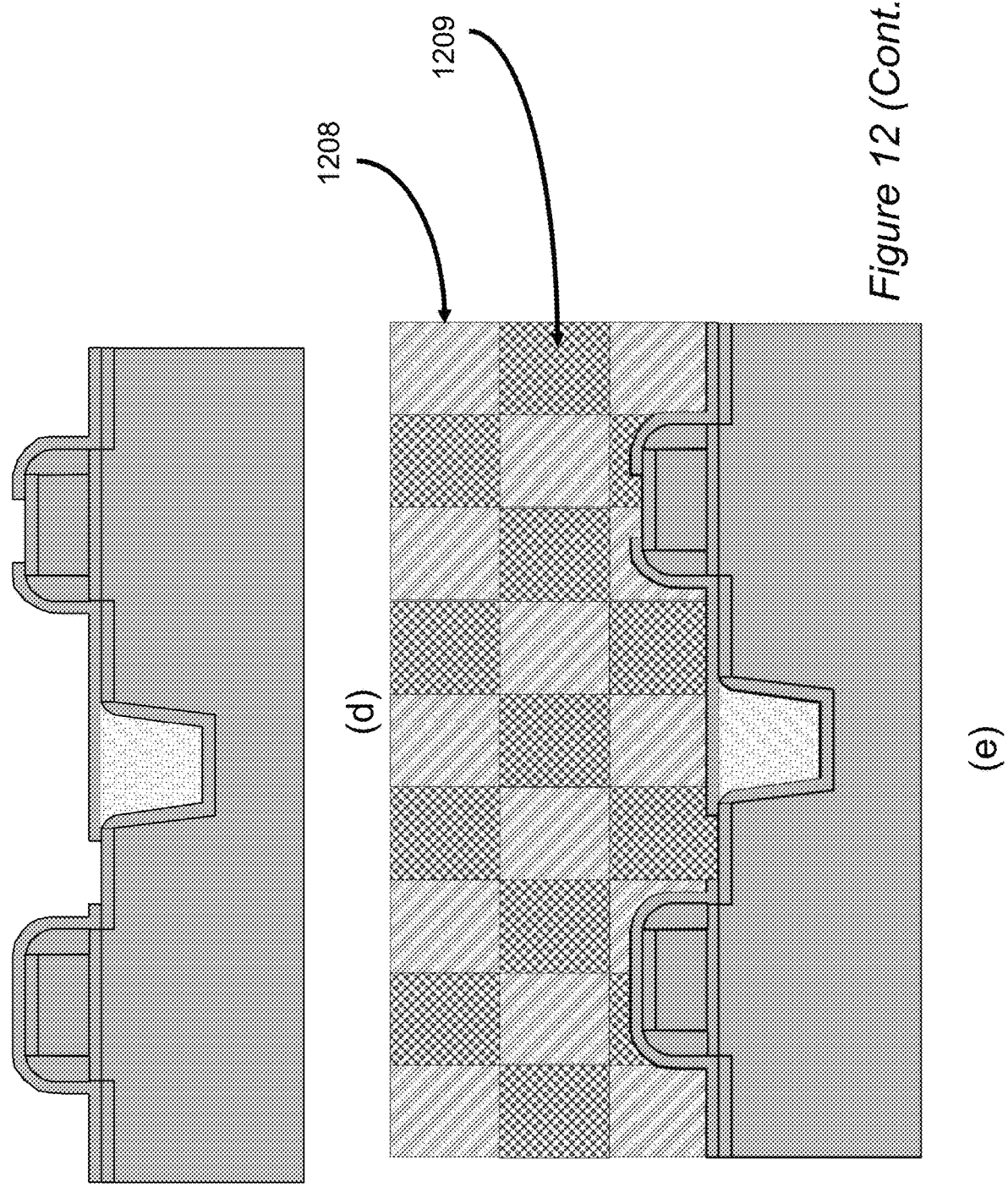
Figure 12:
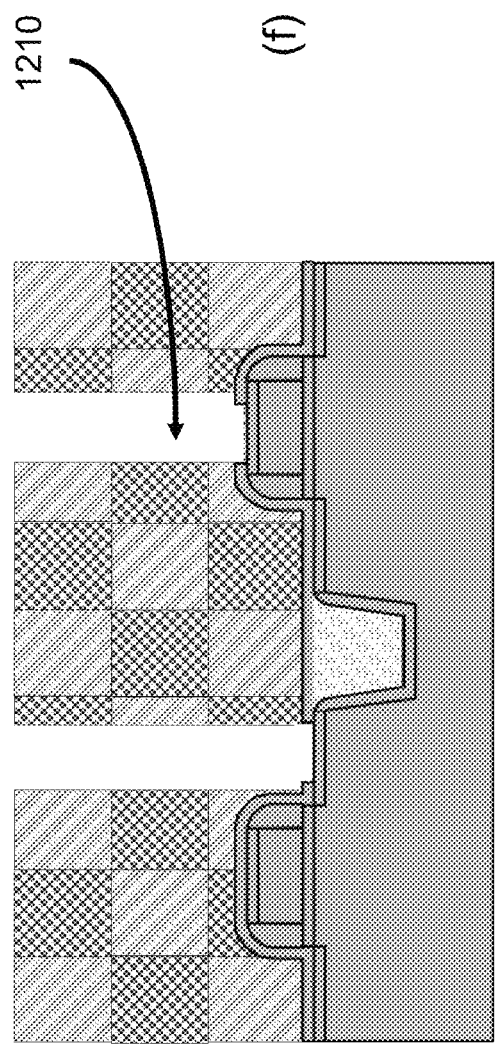
Figure 12:
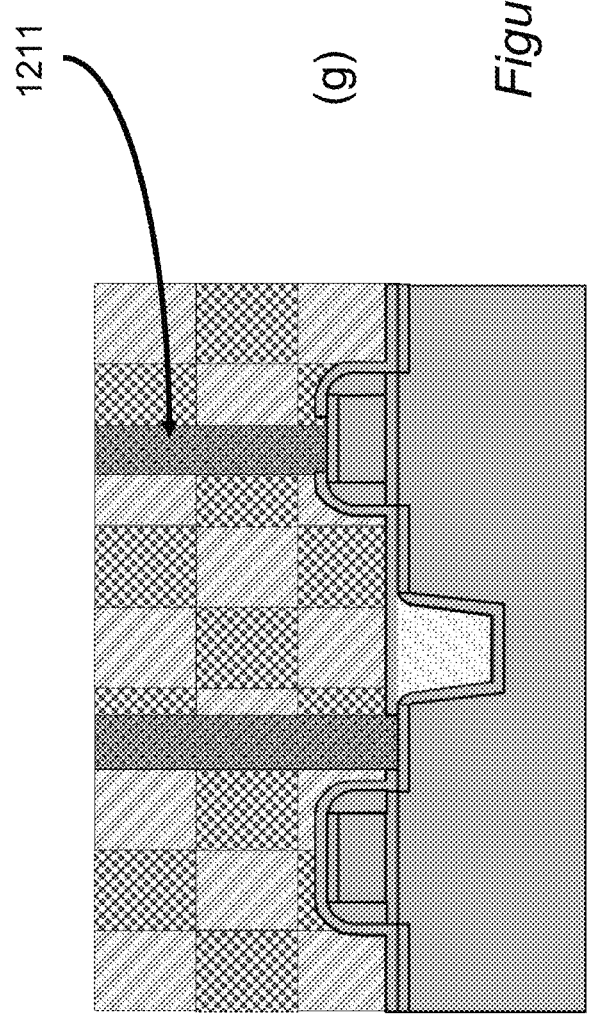
Figure 12:
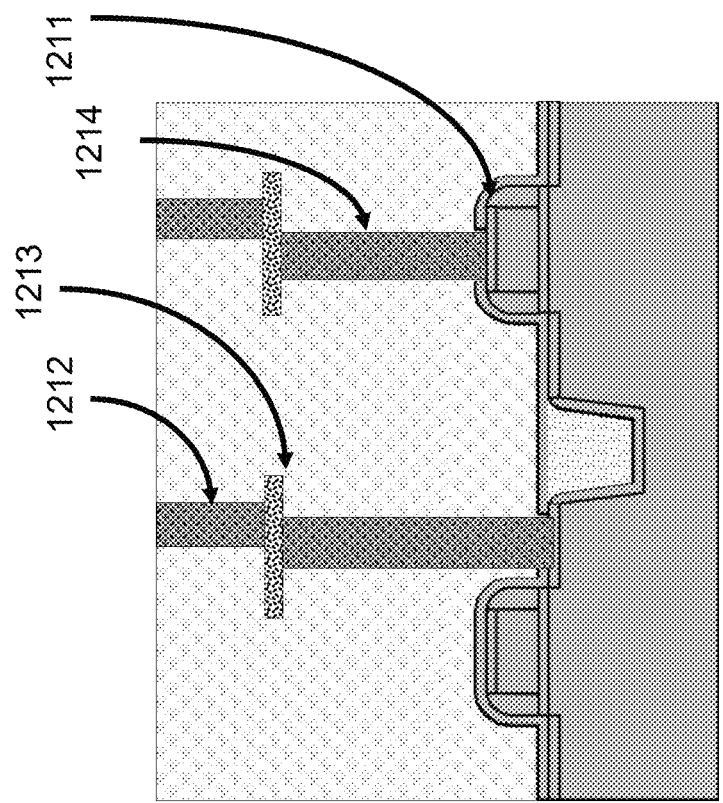
Figure 12:
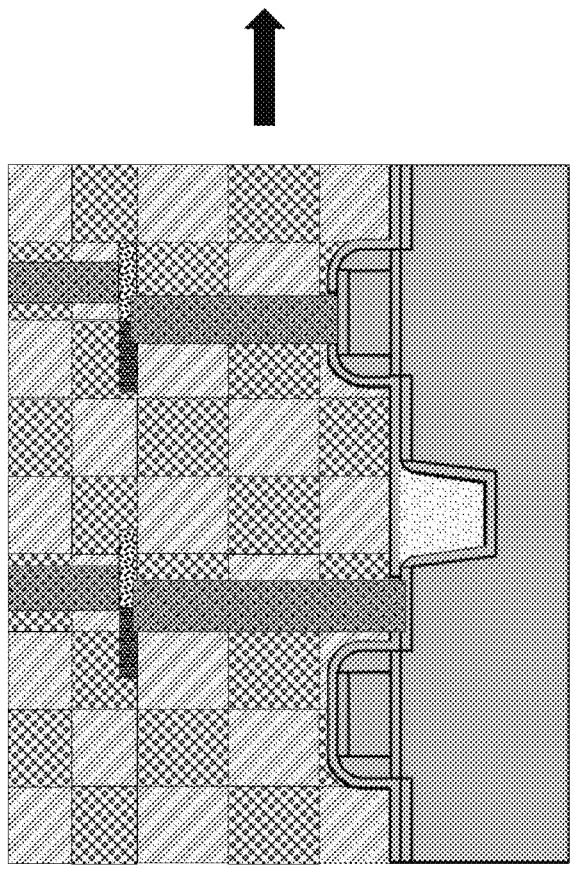
Figure 12:
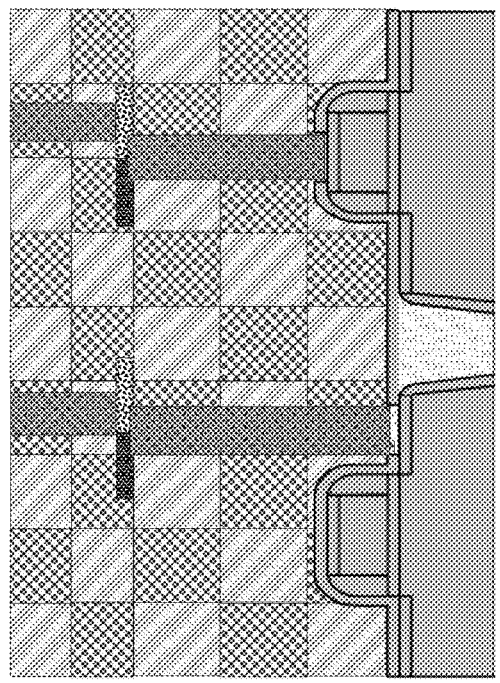
Figure 12:
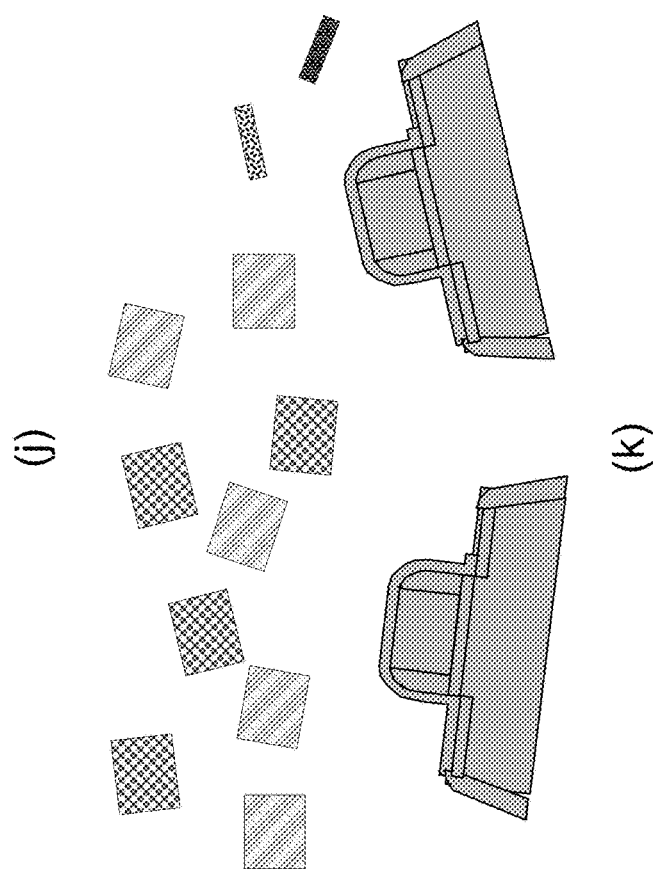

FIG. 12 illustrates a process flow for fabricating a decomposable apparatus of this invention with electrical MOSFET (metal-oxide-semiconductor field-effect transistor) functions.

DETAILED DESCRIPTIONS OF THE INVENTION

The present invention in general relates to a class of innovative decomposing apparatus which utilizes building blocks and/or sub-components integrated with decomposable materials using the state-of-the-art micro-electronics technologies and processes. In this innovative approach, building blocks of medical apparatus, instruments, or drug carriers are comprised of at least two materials where at least one material can be decomposed (or disintegrated) which will result in disintegration of the building block into much smaller pieces (for example, as small as 0.1 micron in size). For example, a building block (for example, a cube) of a size of 100 microns×100 microns×100 microns in volume can be decomposed into smaller pieces of 0.1 micron×0.1 micron× 0.1 micron in volume. Meanwhile, because the surface area is increased greatly, the disintegrated micro or nano particles exhibits quite different chemical/physical properties with respect to the same macro object, and they are much more chemically reactive and prone to be degradable. The decomposition (or disintegration) can be triggered by contacting with a desired solution, gas, or solid. A decomposition (or disintegration) can also be triggered by an external signal. With this disclosed, innovative approach, many innovative, miniaturized medical devices, instruments, apparatus, and carriers can be more effectively and broadly utilized in existing and future medical applications in vivo, enabling more design options, treatment capabilities, and more materials for in vivo medical applications.

One aspect of the present invention relates to decomposing or decomposable apparatus for the purpose of disintegrating and decomposing in vivo (e.g., in a human being, an organ, or a tissue). Each apparatus includes at least one sub-component and at least one decomposable material. The sub-component is a functional component which can be, for example but are not limited to, a drug, a medical kit, a micro-disease detection system, or an auto-navigation system. The decomposable material can be poly(lactide-co-glycolide), poly(lactide), poly(L-lactic acid), poly(D,L-lactic acid), polyglycolic acid, polyanhydrides, poly(ortho ethers), polyamino acids, engineered artificial proteins, natural proteins, biopolymers, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, or a biological material.

The apparatus of this invention and those fabricated by the methods of this invention may have a wide range of designs, structures, functionalities, and features. Specific examples of the above described apparatus with decomposition and disintegration features include, but are not limited to, voltage comparators, four-point probes, calculators, logic circuitries, memory units, micro-cutters, micro-hammers, micro-shields, micro-dyes, micro-pins, micro-knives, micro-needles, micro-thread holders, micro-tweezers, micro-optical absorbers, micro-mirrors, micro-wheelers, micro-filters, micro-choppers, micro-shredders, micro-pumps, micro-absorbers, micro-signal detectors, micro-drillers, micro-suckers, micro-testers, micro-containers, micro-injectors, signal transmitters, signal generators, friction sensors, electrical charge sensors, temperature sensors, hardness detectors, acoustic wave generators, optical wave generators, micro-heaters, heat generators, micro-refrigerators, and charge generators. In addition to the methods of this invention, these apparatus can also be fabricated by other methods as known in the art or described elsewhere, e.g., in PCT/US2010/049298, PCT/US2011/024672, U.S. Ser. No. 12/416,280, PCT/US2011/042637, and PCT/US2010/041001, the contents of all of which are incorporated herein by reference in their entireties.

In some embodiments, the decomposable materials are combinations of decomposable materials and other micronized materials that are not capable of decomposing. The other materials, for example, glasses, or ceramics are fabricated into micro-sizes. The materials with such sizes, even though are not capable of degradation, can be removed from the human bodies easily.

As a key component of the apparatus, the decomposable material shall be capable of breaking down into smaller pieces or decomposing under given conditions, e.g., in the presence of an external signal. Such an external signal can be, for instance, an electric, magnetic, electromagnetic, thermal, optical, acoustical, biological, chemical, electro-mechanical, electro-chemical, electro-chemical-mechanical, bio-chemical, bio-physical, bio-physical-chemical, physical-chemical, bio-mechanical, bio-electro-mechanical, bio-electro-chemical, bio-electro-chemical-mechanical, physical, or mechanical signal. Examples of the electronic property include, but are not limited to, surface charge, surface potential, resting potential, action potential, electrical voltage, electrical current, electrical field distribution, electrical charge distribution, electric dipole, electric quadruple, three-dimensional electrical or charge cloud distribution, electrical properties at telomere of DNA and chromosome, dynamic changes in electrical properties, dynamic changes in potential, dynamic changes in surface charge, dynamic changes in current, dynamic changes in electrical field, dynamic changes in electrical voltage, dynamic changes in electrical distribution, dynamic changes in electronic cloud distribution, or impedance. Examples of the thermal property include, but are not limited to, temperature or vibrational frequency. Examples of the optical property include, but are not limited to, optical absorption, optical transmission, optical reflection, optical-electrical property, brightness, or fluorescent emission. Examples of the chemical property include, but are not limited to, pH value, chemical reaction, bio-chemical reaction, bio-electro-chemical reaction, reaction speed, reaction energy, oxygen concentration, oxygen consumption rate, ionic strength, catalytic behavior, or bonding strength. Examples of the physical property include, but are not limited to, density or geometric size; the acoustic property is frequency, speed of acoustic waves, acoustic frequency and intensity spectrum distribution, acoustic intensity, acoustical absorption, or acoustical resonance. Examples of the mechanical property include, but are not limited to, internal pressure, hardness, shear strength, elongation strength, fracture stress, adhesion, mechanical resonance frequency, elasticity, plasticity, or compressibility.

Consequently, the sub-component integrated onto the decomposable material is released from the apparatus in vivo (e.g., in a human body) to start the treatment. One example of such an apparatus comprises a drug integrated onto a decomposable material. When the apparatus breaks down or the material degrades, the drug is released from the apparatus for the treatment of a disease.

In some embodiments, the decomposable material decomposes in a controlled manner, e.g., over a desired period of time. There is no limitation of a minimum or maximum time period in current invention. The desired period of time depends on the demands in different surgeries or treatment. Some examples of such a time period include, for example, from a couple seconds to a couple weeks.

In some embodiments, the apparatus comprises a sub-component and a decomposable material, wherein they are integrated and arranged in one layer. When applying an external signal to the apparatus, the decomposable material breaks down and consequently releases the sub-component for further treatment. The geometric dimension of the drug is decided during fabrication process of such an apparatus.

Yet in some other embodiments, the current invention includes two sub-components and a decomposable material, wherein they are integrated and arranged into either one layer or two layers. The two sub-components can be, for example, a drug, a medical kit, a micro-disease detection system, or an auto-navigation system, respectively. They can be both drugs of different kinds. When an external signal is applied to the decomposable material, the two sub-components release from the apparatus for treatment of a disease, or detection of a disease.

One embodiment of such an apparatus comprises at least one of the sub-components being a micro-disease detection system. The system can detect a disease in vivo (e.g., in a human body) and send a signal to the apparatus. Consequently, the signal will activate the decomposition of the decomposable material and thus led to the result of breakdown of the apparatus.

In yet other embodiment of current invention, the apparatus comprises two layers of decomposable materials packaging two or more drugs within the layers. One example of such an invention comprises an inner layer of decomposable material which packaged a first drug inside of the layer, and an outer layer of decomposable material packaged a second drug between the outer layer and the inner layer of decomposable materials. The first and second drugs can be same or different.

When receiving an external signal, i.e., an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal, the outer layer of decomposable material may break down and release the second drug for further treatment.

The inner layer of decomposable material will break down afterward when it also receives an external signal as described above. The first drug packaged in the inner layer will then be released for further treatment.

Since the two layers are decomposed at different times, consequently, the two drugs are released at different times.

Yet another embodiment of current invention further comprises at least two apparatus as mentioned above integrated together, wherein at least four drugs are packaged within the apparatus. At least two drugs are packaged within inner layers of decomposable materials, and at least two drugs are sandwiched between outer layers and inner layers of decomposable materials. The drugs packaged in the same layers can be same or different.

Still another embodiment of current provides an apparatus comprising two layers of decomposable materials, two drugs packaged within each layer, and at least one sub-component integrated onto one or two layers of the decomposable materials. The sub-component can include, but are not limited to, a micro-disease detection system, or an auto-navigation system. When the micro-disease detection system is integrated onto the inner or outer layer of the decomposable material, it will send an external signal to the layer and thus activate the decomposition. The corresponding layer then breaks down and thus releases the drug being packaged.

One further aspect of current invention provides a fabricating process of a decomposing apparatus, comprising providing a substrate, depositing a first material onto the substrate, depositing a photoresist onto the first material. Examples of suitable photoresist includes, but are not limited to, methacryl, acryl, α-(trifluoromethyl)-acryl, norbornene, vinyl, styrene monomers with fluoroalcohol.

The photoresist is further exposed to and developed using a light with a desired wave length, an electromagnetic wave, electron, or an ion beam.

Then the first material is etched (e.g., by dry etch, wet etch, or vapor etch) using the remaining photoresist as a hard mask, to deliver the shape of the remaining photoresist to the first material.

A second material can then be deposited onto the first material and the substrate, and planarized (e.g., by chemical polishing, mechanical polishing, or chemical-mechanical polishing) to stop on the layer of the first material. Alternatively, the second material can be etched back to the top of the first material, with the second material remaining in the portions of the recessed areas in the first material.

Finally, the substrate is removed, giving rise to decomposable apparatus comprising the first and second materials which may be alternatively arranged or configured.

The first material may comprise a drug, a medical kit, a micro-disease detection system, or an auto-navigation system.

Sequentially, the photoresist is developed to remove portion of the photoresist, leaving the remaining part of photoresist a desired shape. The photoresist is used as a hard mask during the planarization of the first material to pass the desired shape to the first material. And then the remaining photoresist is removed.

The fabrication process may comprise repeating the above-described steps to form one or more layers of integrated sub-components and decomposable material.

The decomposable apparatus thus fabricated may be activated by an external signal and decompose. Examples of a suitable signal include an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal.

The apparatus thus fabricated breaks down into small pieces in the presence of above mentioned signal.

Set forth below are several examples of apparatus of this invention containing at least one sub-component and at least one decomposable material, and of their fabrication process. These examples are provided only for illustration of some aspects of this invention and should not be interpreting as limiting in any way.

Figure 1:
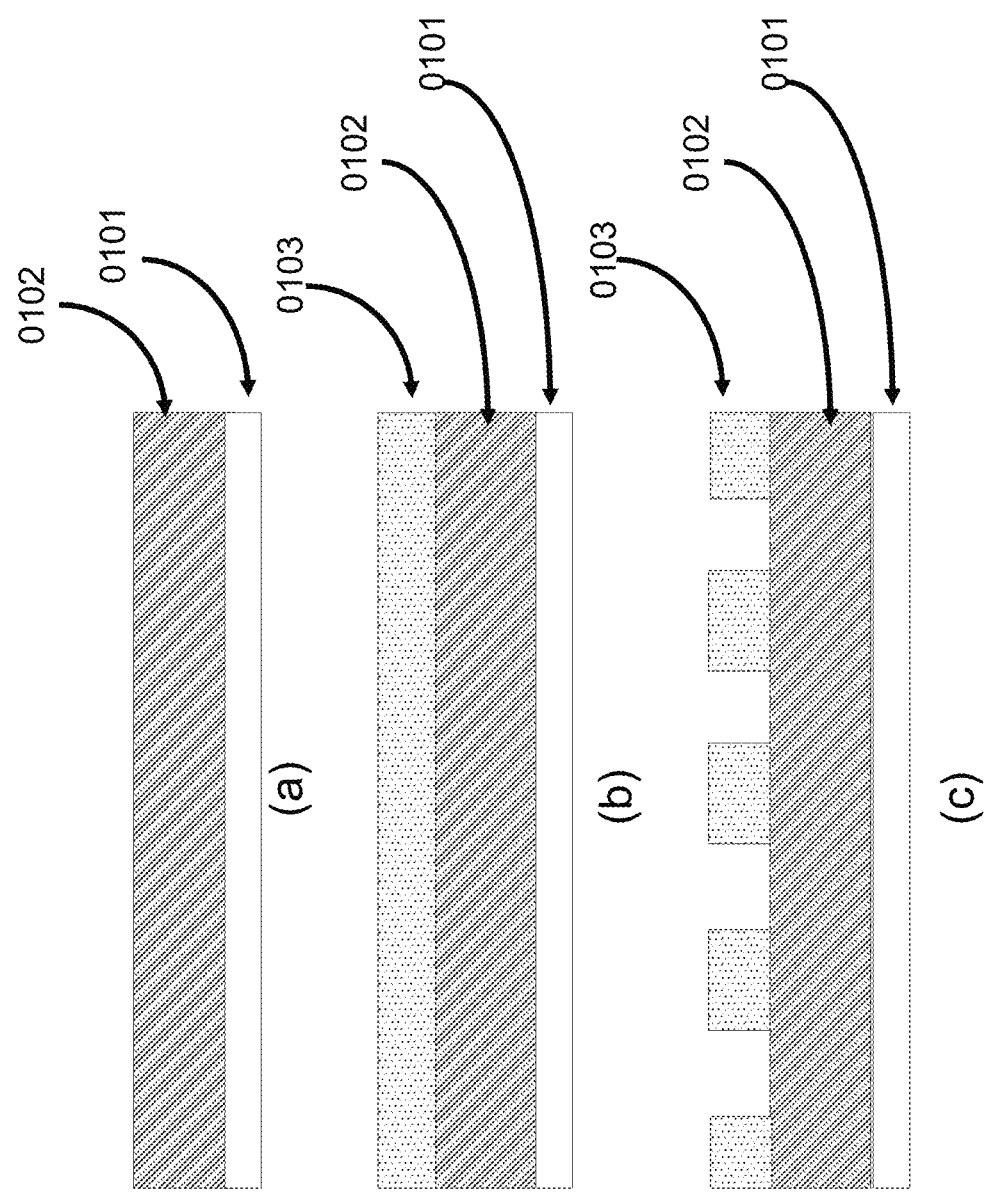
FIG. 1 shows a novel fabrication process of a decomposing apparatus, wherein micro-electronic technologies and processes are used during the fabrication.
Figure 1:
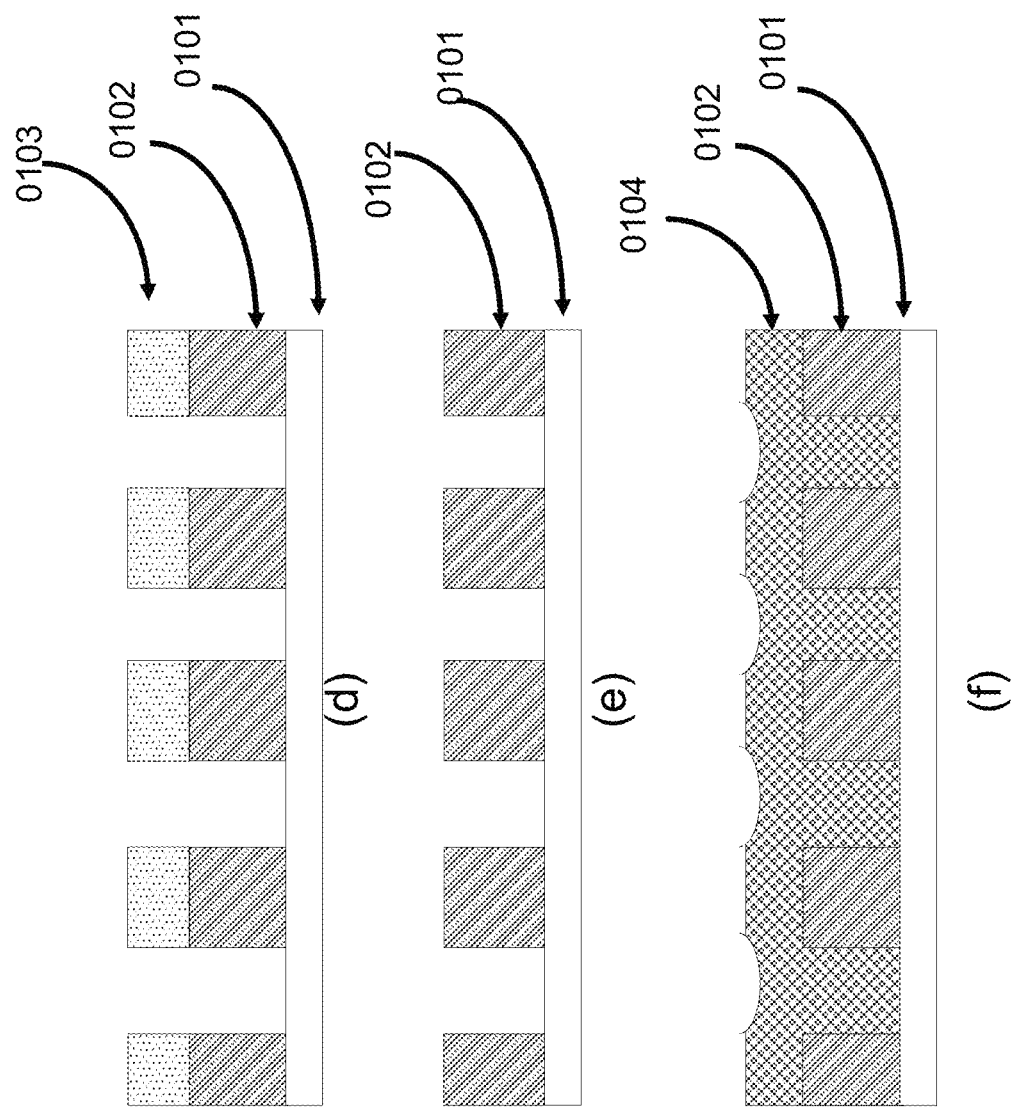
Figure 1:
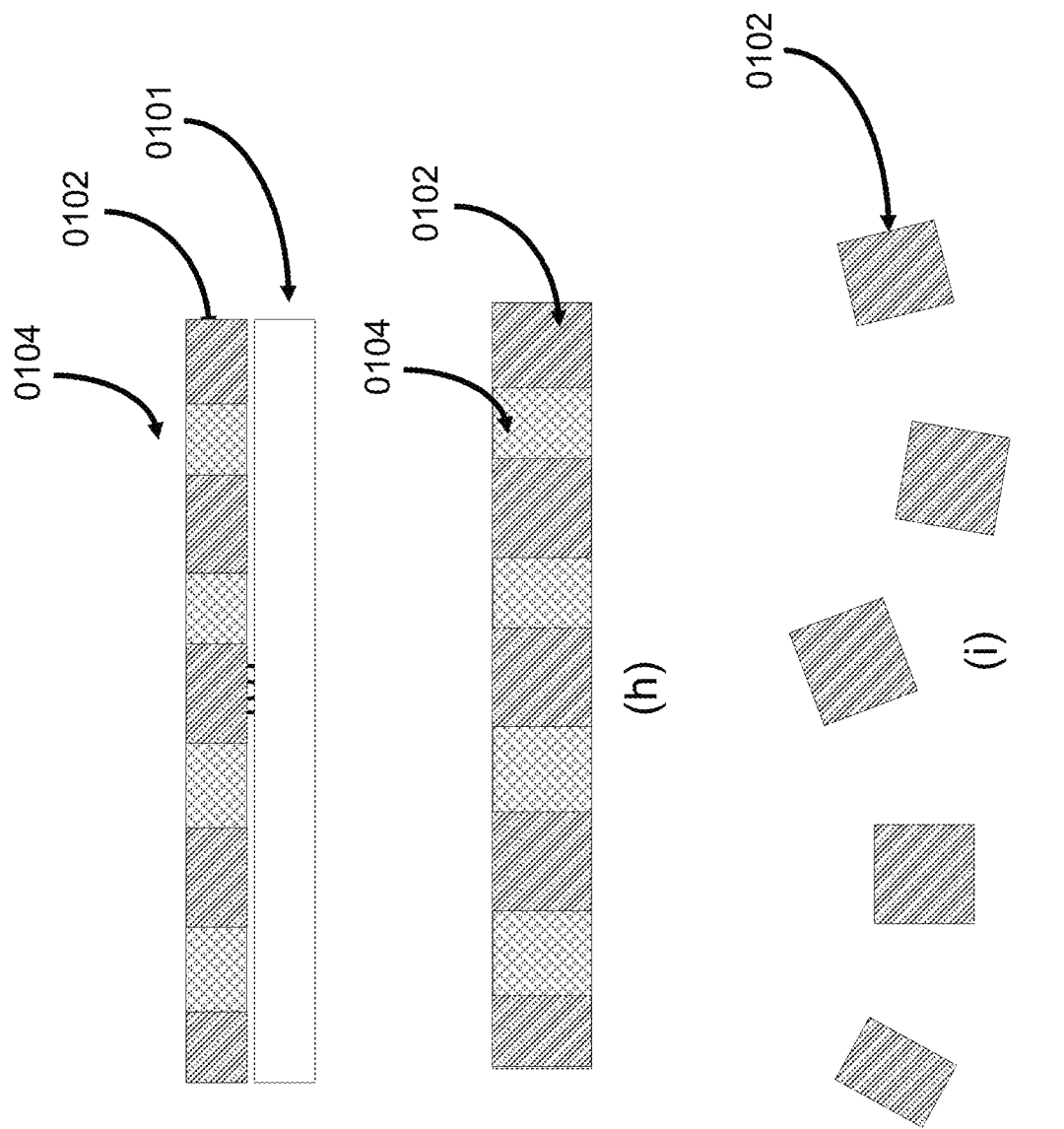

FIG. 1 illustrates a novel fabrication process of a decomposing apparatus. A material 0102 is deposited onto the substrate 0101 (FIG. 1(a)). A photoresist 0103 is then deposited onto material 0102 (FIG. 1(b)) and then exposed and developed using lights with a specified wave length (FIG. 1(c)). The remaining portion of photoresist 0103 is used as a hard mask when etching material 0102 to form a desired shape (FIG. 1(d)). The photoresist 0103 can then be removed from material 0102 (FIG. 1(e)). A material 0104 is then deposited onto material 0102 and substrate 0101 (FIG. 1(f)). Material 0104 can then be planarized (e.g., by a chemical, mechanical, or chemical-mechanical polishing process) (FIG. 1(g)). Finally substrate 0101 is removed (FIG. 1(h)) to result in a decomposable apparatus. When activated by an external signal, material 0104 will decompose and consequently, the apparatus will break down into pieces, material 0102 will be released from the apparatus.

A decomposable apparatus comprising at least two sub-components can be formed by repeating the steps as shown in FIG. 1.

Figure 2:
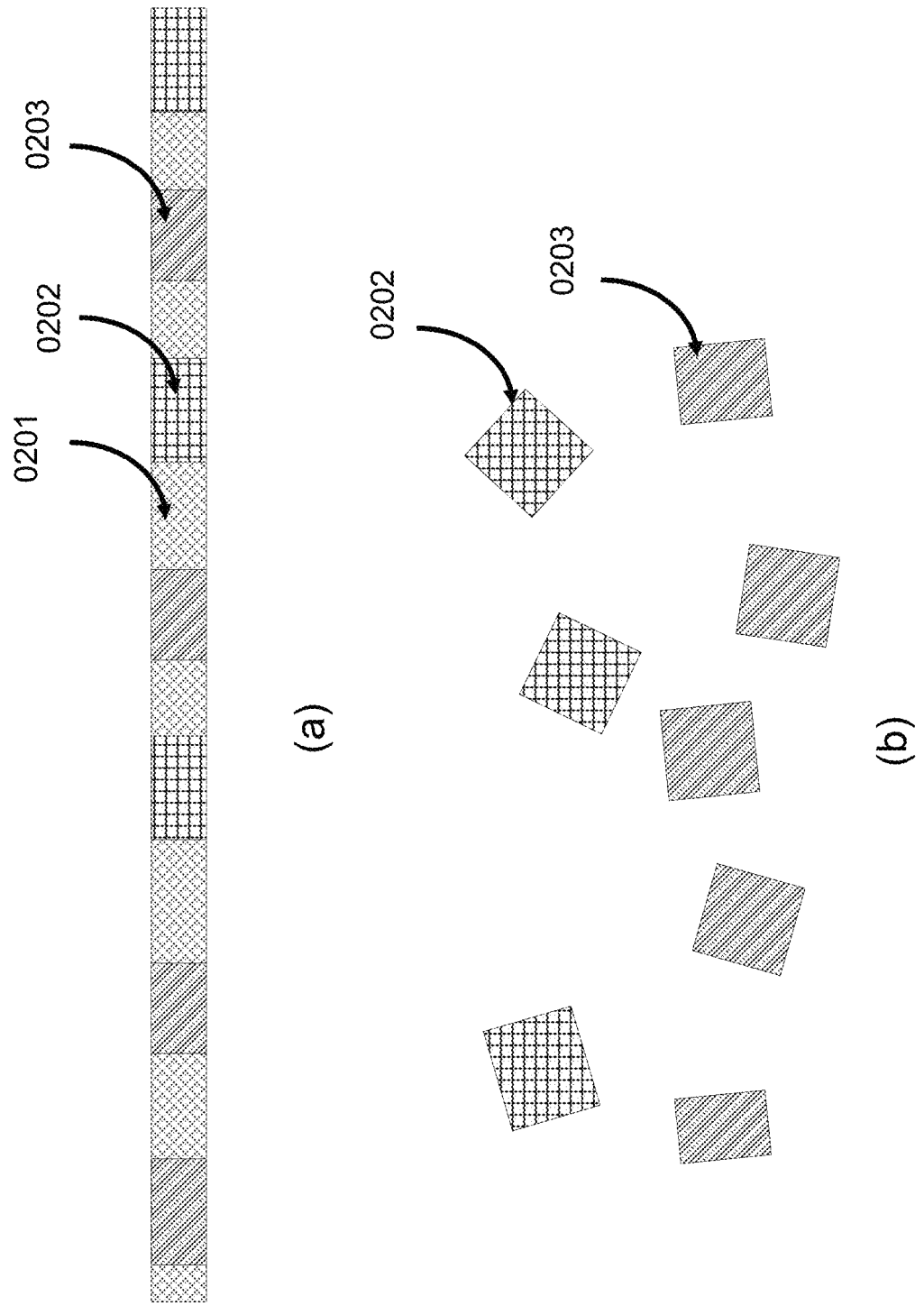
FIG. 2 shows a novel decomposing apparatus with two drugs integrated onto a decomposable material, wherein the decomposing apparatus dissolves and releases the two drugs in vivo in human bodies.

FIG. 2 shows another novel decomposing apparatus comprising materials 0201, 0202 and 0203 (FIG. 2(*a*)). Material 0201 is a decomposable material which decomposes in the presence of an external signal. Consequently, materials 0202 and 0203 are released from the apparatus as small pieces (FIG. 2(*b*)).

Figure 3:
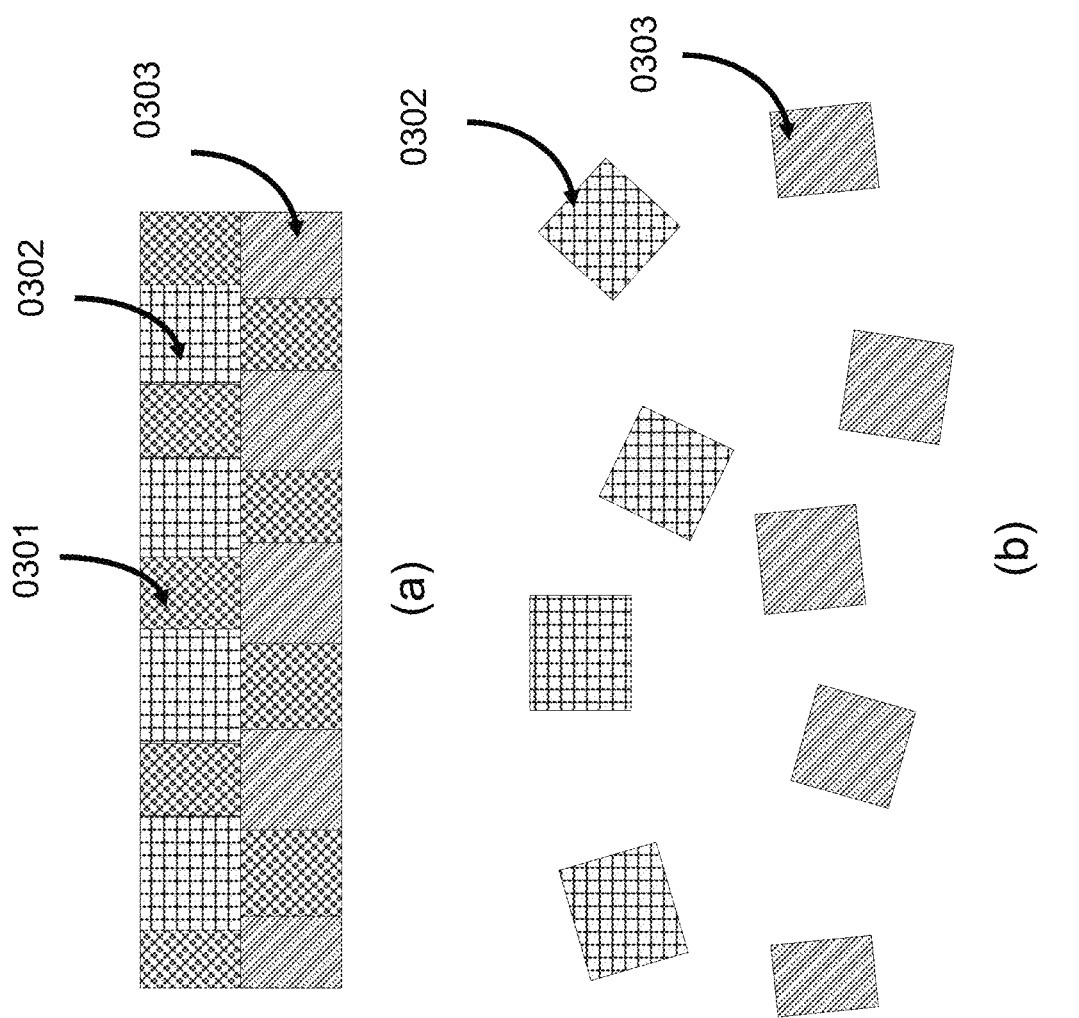
FIG. 3 shows another novel decomposing apparatus with two drugs integrated with a decomposable material, wherein the two drugs are arranged in two layers.

Even more complex apparatus can be formed by repeating the steps shown in FIG. 1. Specifically, as illustrated in FIG. 3, an apparatus can be arranged into two layers. Materials 0301, 0302 and 0303 are integrated onto each other and arranged into two layers. Material 0301 is a decomposable material which can decompose in the presence of an external signal. Materials 0302 and 0303 are thus released from the apparatus as small pieces. The geometric dimensions of materials 0302 and 0303 are decided by the shape of the remaining photoresist during exposure process.

Figure 4:
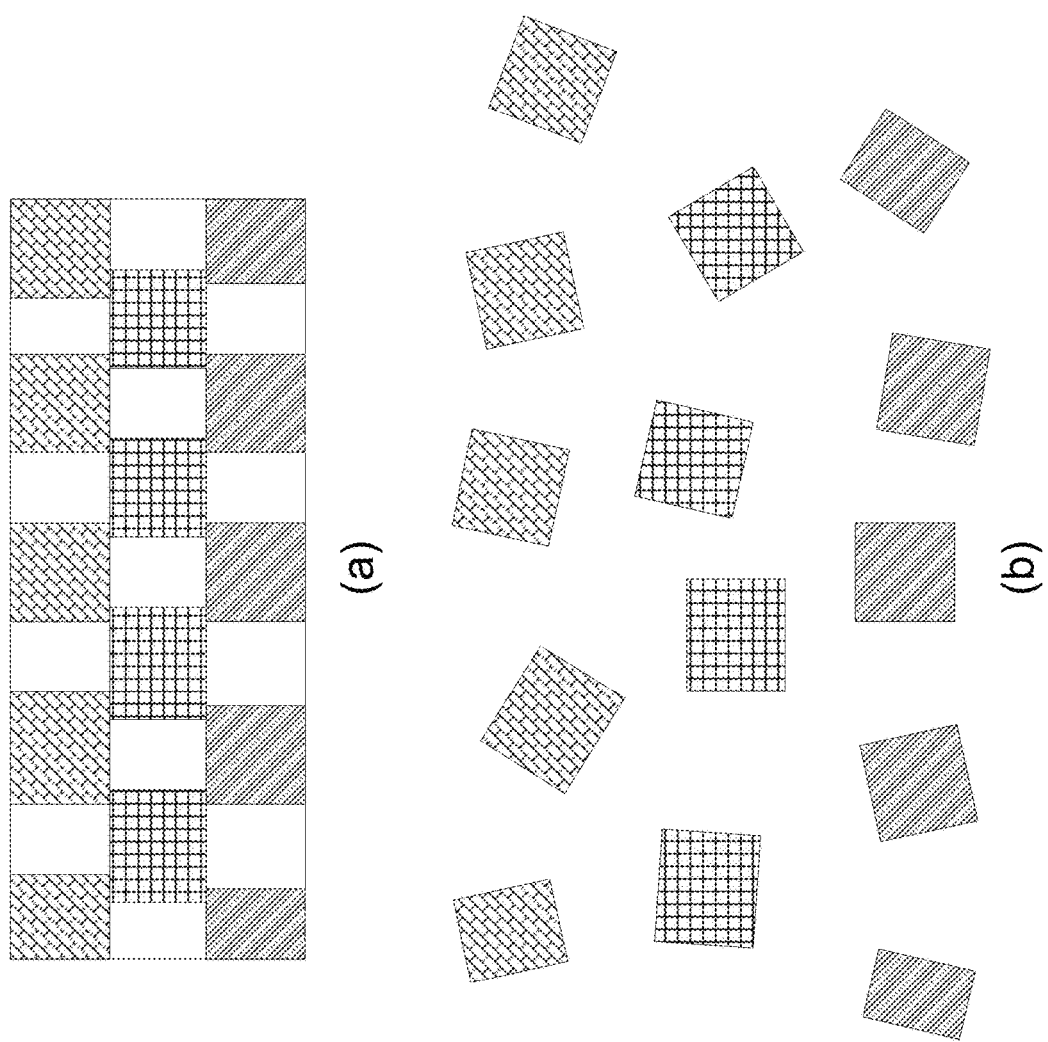
FIG. 4 shows yet another decomposing apparatus wherein three drugs are integrated onto a decomposable material and arranged in three layers.

Another example of this invention provides a decomposing apparatus with three layers (FIG. 4(*a*)) wherein at least three materials are integrated onto the decomposable material and arranged into three decomposable layers. Once the decomposable material decomposes, the three materials will be released at small pieces (FIG. 4(*b*)).

As a principle, the current invention can provide even more complex apparatus with more layers of decomposable material integrating with different materials.

Figure 5:
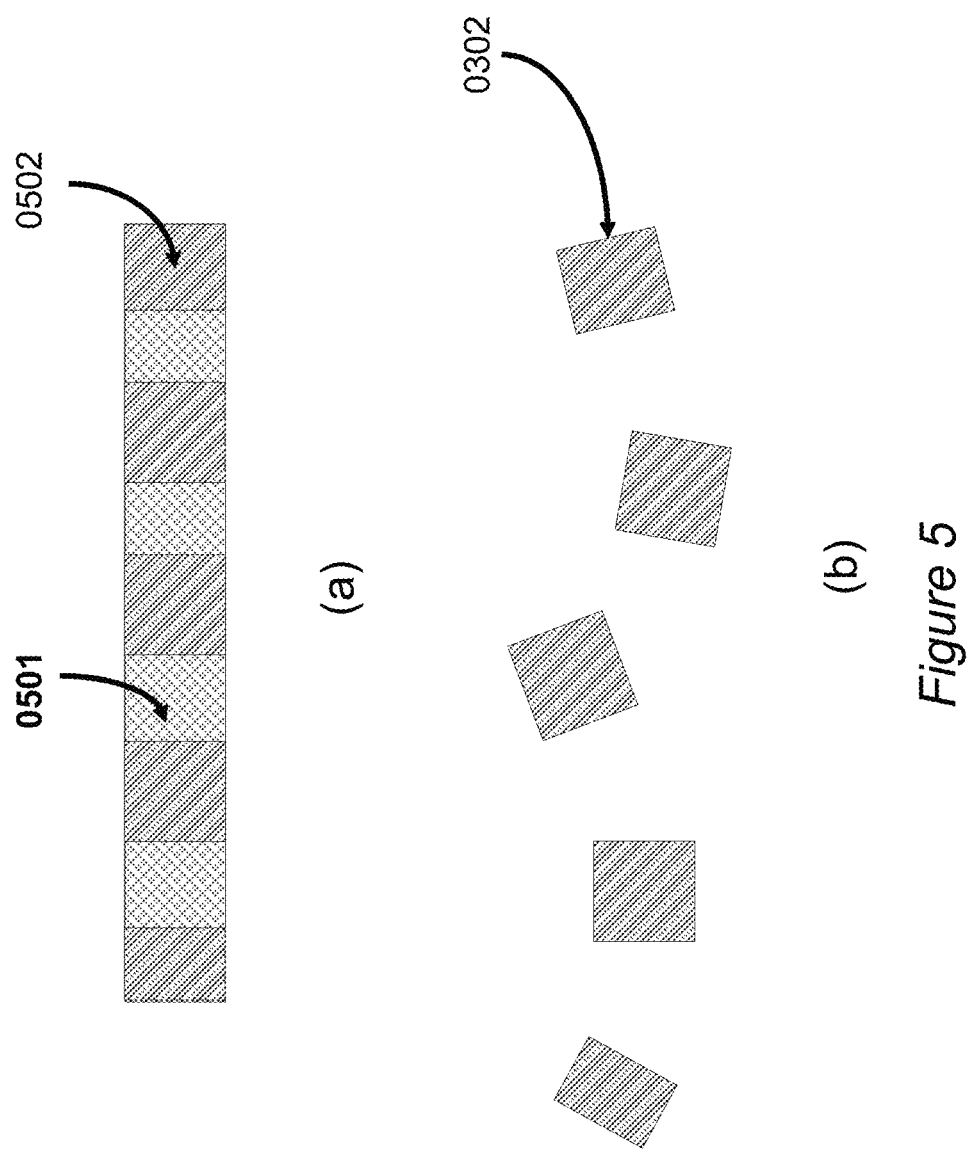
FIG. 5 shows a nano-drug delivery apparatus with nano-drug particles integrated onto a decomposable material. The nano-drug particles will be released when the decomposable material dissolves.

One example of the current invention is a nano-drug delivery apparatus as shown in FIG. 5. Here, a decomposable material 0501 is integrated with a nano-drug 0502 to form an apparatus of current invention (FIG. 5(*a*)). The decomposable material 0501 is capable of dissolving in the presence of an external signal, e.g., an electric, magnetic, electromagnetic, thermal, optical, acoustical, biological, chemical, electro-mechanical, electro-chemical, electro-chemical-mechanical, bio-chemical, bio-mechanical, bio-electro-mechanical, bio-electro-chemical, bio-electro-chemical-mechanical, physical, or mechanical signal. The nano-drug 0502 is then released for treatment of a disease.

Figure 6:
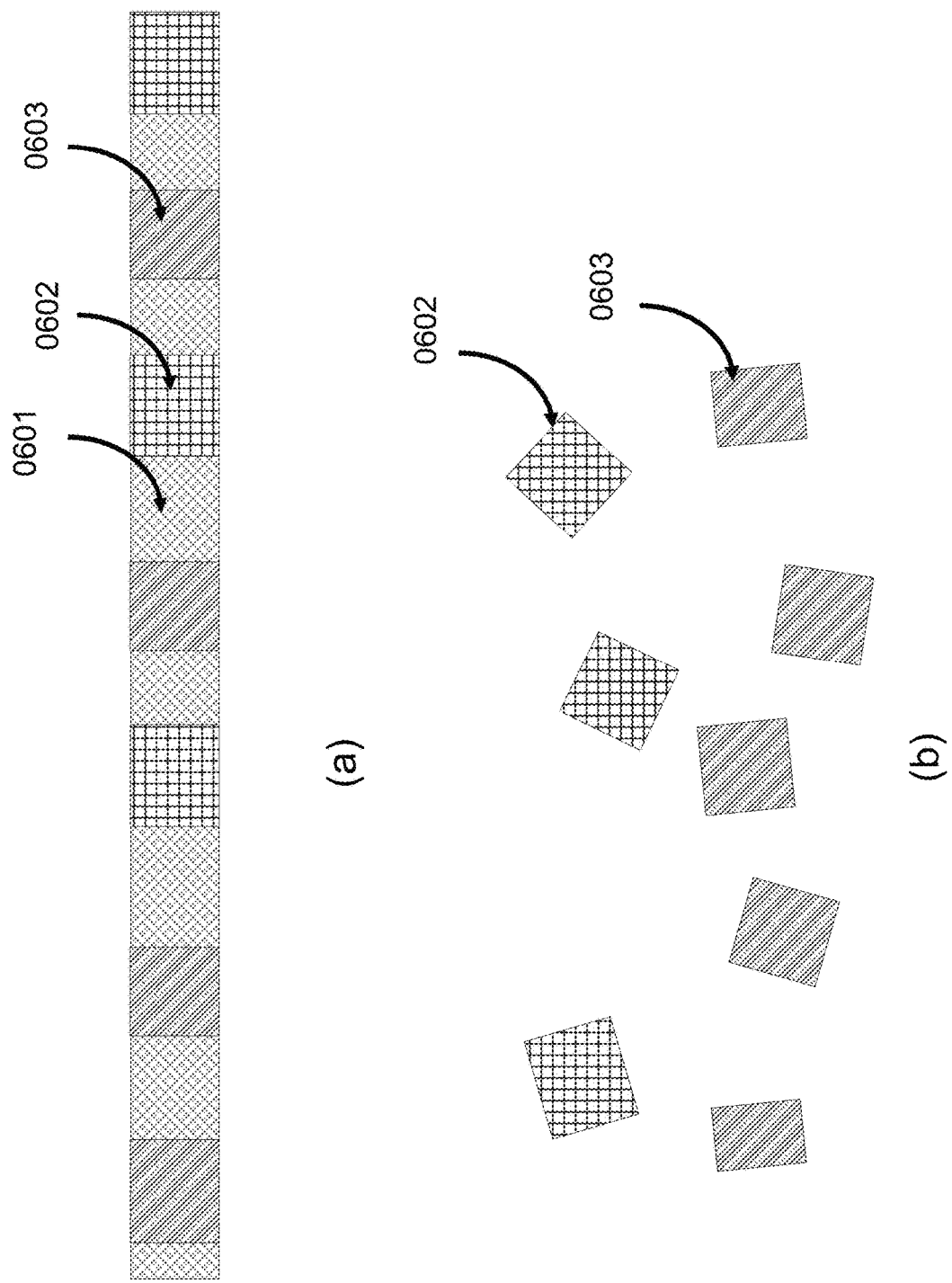
FIG. 6 shows yet another nano-drug delivery apparatus, wherein two drugs are integrated onto a decomposable material. The two drugs are released when the decomposable material dissolves.

FIG. 6 illustrates another example of a nano-drug delivery apparatus. In this example, nano-drugs 0602 and 0603 are integrated onto decomposable material 0601 and arranged at one layer (FIG. 6(*a*)). The drugs 0602 and 0603 are different drugs. Decomposable material 0601 will dissolve in the presence of an external signal. Consequently, nano-drugs 0602 and 0603 are released from the apparatus for treatment of a disease (FIG. 6(*b*)).

Figure 7:
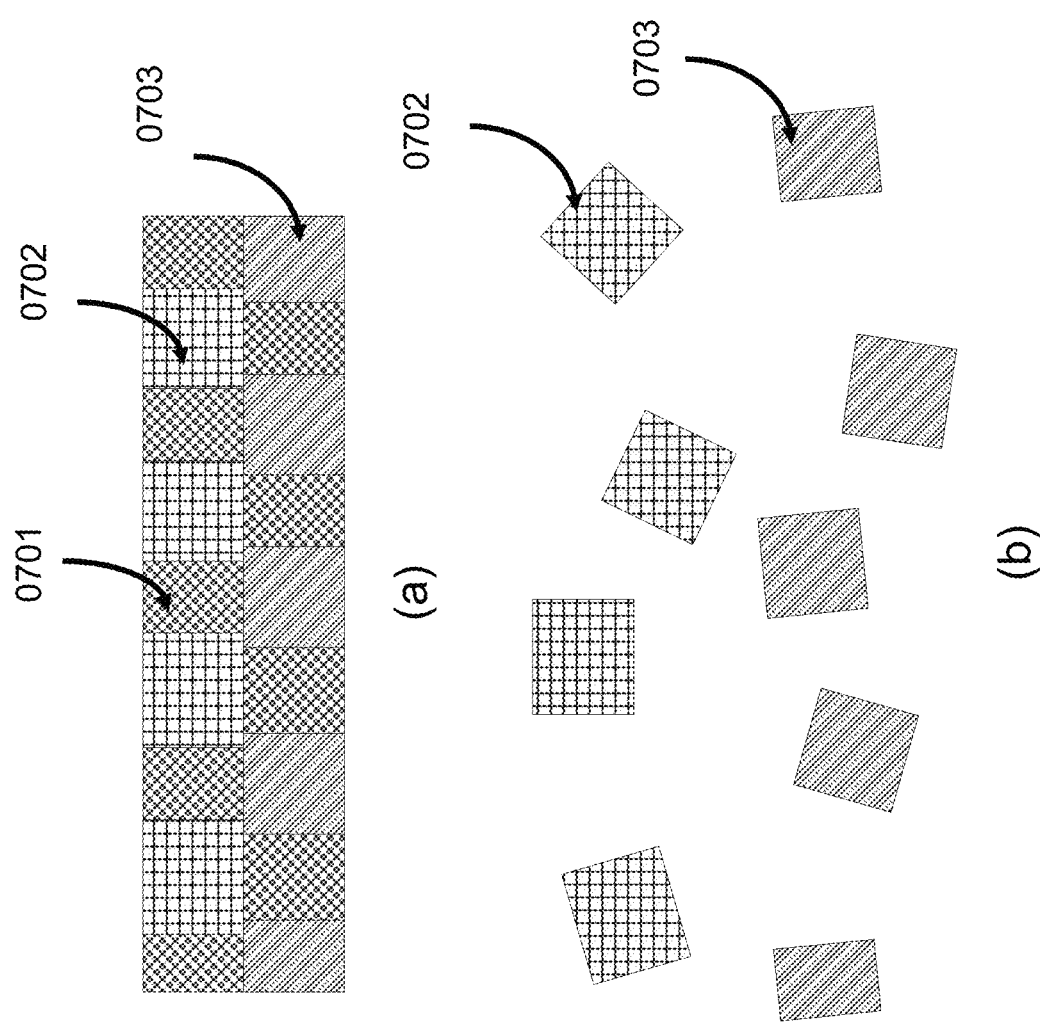
FIG. 7 shows a nano-drug delivery apparatus wherein two drugs are integrated onto a decomposable material in two layers. The drugs are released from the apparatus when the decomposable material dissolves.

Such an apparatus can be extended as a two-layer apparatus as illustrated in FIG. 7. In this example, nano-drugs 0702 and 0703 are integrated onto decomposable material 0701 and arranged as two layers. Nano-drug 0702 can be the same or different as nano-drug 0703. Decomposable material 0701 dissolves when an external signal is applied to the apparatus, then nano-drugs 0702 and 0703 are released as small pieces for treatment of a disease.

Understandably, such an apparatus can include additional multiple layers of decomposable material integrated with other materials, and multiple types of drugs in different layers.

FIG. 8 shows another embodiment of this invention. In this embodiment, the apparatus for carrying drugs as shown in FIG. 8(*a*) comprises a drug 0803, an inner layer of decomposable material 0804, a drug 0801, and an outer layer of decomposable material 0802. The inner layer of decomposable material packages drug 0803 inside of the layer. Drug 0801 is sandwiched between the inner and outer layers of the decomposable material. It can be the same or different as drug 0803 (FIG. 8(*a*)).

When using the apparatus in vivo of a human body, the outer layer of decomposable material decomposes in the presence of an external signal. Drug 0802 is firstly released from the apparatus (FIG. 8(*b*)). In the same way, the inner layer of decomposable material will decompose in the presence of an external signal, and drug 0803 will be released.

Since the drug 0801 and 0803 are located in different layers, they are released at different times. Drug 0801 can be the same or different as drug 0803.

FIG. 8(*c*) is another example of this invention comprising two inner layers of decomposable materials 0816 and 0817, which packages drugs 0812 and 0814, respectively. The outer layer of decomposable material 0815 is divided into two parts, wherein two drugs 0811 and 0813 are sandwiched between layer 0815 and layers 0816 and 0817, respectively. Drugs 0811 and 0813 can be same or different, and drugs 0812 and 0814 can also be same or different.

In principle, the apparatus of current invention can include multiple compartments and multiple inner layers.

FIG. 9 illustrates another novel apparatus of this invention comprising an inner layer of decomposable material 0904 and an outer layer of decomposable material 0902. Drug 0903 is packaged in layer 0904, and drug 0901 is sandwiched between layers 0904 and 0902. Micro-disease detection systems 0905 and 0906 are integrated onto the inner and outer layers 0904 and 0902, respectively (FIG. 9(*a*)).

The detection system 0906 can detect diseases in vivo (e.g., in a human body). It will then send a signal to the layer 0902 and then activate its decomposition, thus releasing the drug 0901. In the same way, detection system 0905 will send a signal to layer 0902 and activate the decomposition of layer 0902, thus releasing drug 0903. Drugs 0901 and 0903 can be same or different. They can be released from the apparatus at different times.

Optionally, an auto-navigation system can be integrated into the apparatus by which the apparatus can be navigated to the lesions and perform treatment.

FIG. 10 illustrates a novel process flow for fabricating a decomposable apparatus of this invention by utilizing microelectronics technologies and processes. In this process, an insulation material 1002 is first deposited onto a substrate 1001 (FIG. 10(*a*)), coated with a photoresist 1003 (FIG. 10(*b*). It is then masking exposed with a light with a specified wave length (e.g., a visible or invisible light), electromagnetic wave, or electron or ion beams, and then being developed (FIG. 10(*c*)).

An etching process is then followed to transfer the pattern from the photoresist to material 1002 (FIG. 10(*d*), and the remaining photoresist is removed (FIG. 10(*e*)) before another insulation material 1004 is deposited (FIG. 10(*e*)). Deposited material 1004 is planarized by polishing (e.g., mechanical polishing, chemical polishing, or chemical mechanical polishing) as shown in FIG. 10(*g*). A conductive material 1005 is then deposited (FIG. 10(*h*)), and then patterned by lithography and etch process (FIG. 10(*i*)).

Another conductive material 1006 is then deposited (FIG. 10(*j*)) and planarized by polishing (e.g., mechanical polishing, chemical polishing, or chemical mechanical polishing) as shown in FIG. 10(*k*). The conductive layer 1006 is then patterned by lithography and etch (FIG. 10(*l*)), followed by depositing the insulating material 1002. (The insulating material can be the same or different with regard to the material used in prior process (FIG. 10(m)). The insulating layer 1002 is planarized by a CMP process (FIG. 10(n)) and then patterned by lithography and etch process (FIG. 10(o)), followed by depositing (FIG. 10(p)) and planarizing by CMP (FIG. 10(q)) of the insulating material 1004, which is different from the material in the same layer.

Then the substrate is stripped (FIG. 10(r)). Hereby, the generic prototype whose insolating layer and conducting layer are both decomposable is then fabricated. It is electrically equivalent to the device illustrated in (FIG. 10(r)), which is composed of a conductive wiring embedded in insulating layer.

By repeating steps b, c, d, e, f, and g as shown in FIG. 10, a decomposable apparatus which comprises multiple (more than 2) types of components can be fabricated. As is shown in FIG. 2(a), the apparatus contains 3 types of components, 0201, 0202, and 0203. As is illustrated in FIG. 2(b), when material 0201 is dissolved at a given condition, the device is decomposed and breaks down into smaller pieces 0202 and 0203. The smaller pieces' geometric shape and dimensions are defined by the mask used when exposure.

When a specific signal is given or being place in a particular environment, or being etched by specific etchant, insulating material 1002, and conductive material 1005 shrinks in its geometric parameter (e.g., size) (FIG. 10(t)), then the apparatus starts to decompose into smaller pieces (FIG. 10(u)).

By repeating the steps illustrated in FIG. 10, more complicated decomposable apparatus comprising multiple (more than 1) decomposable insulating and conductive layers or materials can be fabricated (FIG. 10(v)).

FIG. 11 illustrates another method for fabricating a decomposable apparatus of this invention. A liner layer 1102 and outer layer 1103 are deposited on the substrate 1101 (FIG. 11(a)). The layer 1103 is then patterned by lithography and etch (FIG. 11(b)), and a liner layer 1104 is selectively deposited around the 1103 pattern (FIG. 11(c)). Another layer 1105 is then deposited (FIG. 11(d)), planarized by CMP (FIG. 11(e)), and the substrate 1101 is then stripped off. Hereby, a decomposable device is fabricated.

After the liner layer 1102 and 1104 are etched or dissolved at specific conditions (FIG. 11(f)), the apparatus decomposes into smaller pieces (FIG. 11(g)).

FIG. 12 illustrates a process flow for fabricating a decomposable apparatus of this invention with electrical MOS-FET functions. On substrate 1205, a trench 1206 is first fabricated by lithography and etch (FIG. 12(b)). Material 1207 is then deposited and planarized (FIG. 12(c)). Then a transistor's source, drain and gate are fabricated by traditional microelectronic processes (FIG. 12(d)). An insolating dielectric is fabricated with novel process as described in FIG. 10, with insolating material 1208 and 1209 being interlaced deposited and patterned (FIG. 12(e)). The contact hole 1210 is patterned by lithography and etch process (FIG. 12(f)) and conducting material 1211 is then deposited to fill the contact hole and subsequently planarized (FIG. 12(g)). 1211 is the transistor's device body (source, drain, and gate); 1212 is the interconnecting VIA; 1213 is interconnecting wiring, and 1214 is interconnecting contact.

By the same process, VIA holes and interconnections can be fabricated (FIG. 12(h)), thus giving a MOS-FET (i.e., metal-oxide-semiconductor field-effect transistor) with interconnections. The apparatus illustrated in FIG. 12(h) is electrically equivalent to the one shown in FIG. 12(i). After substrate grinding, the decomposable MOS-FET is fabricated (FIG. 12 (j)), and then the apparatus can be decomposed into smaller pieces when sub-components dissolve or shrink at specific conditions.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All publications or patent application referenced herein are incorporated by reference in their entireties.

What is claimed is:

1. A decomposing apparatus, comprising a first sub-component and a first micro device which comprises a decomposable material and is integrated with the first sub-component; wherein the apparatus comprises a layer with an interlaced structure, and the interlaced structure comprises straight-sided building blocks and is formed by at least two materials, one being the decomposable material, and the layer decomposes into smaller pieces upon the decomposition of the decomposable material; wherein the layer is included by the first micro device, or comprises the first micro device and the first sub-component;
wherein the interlaced structure comprises at least two types of the building blocks, with one type of the building blocks surrounded by other types of the building blocks, and when one type of the building blocks decomposes or changes geometric parameter, the layer with the interlaced structure decomposes into smaller pieces.

2. The apparatus of claim 1, wherein the sub-component comprises a drug, a medical kit, a micro-disease detection system, or an auto-navigation system.

3. The apparatus of claim 1, wherein the decomposable material comprises poly(lactide-co-glycolide), poly(lactide), poly(L-lactic acid), poly(D,L-lactic acid), polyglycolic acid, polyanhydride, poly(ortho ether), polyamino acid, engineered artificial protein, natural protein, biopolymer, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite or mixture thereof.

4. The apparatus of claim 1, wherein the decomposable material is activated to decompose by a signal, an agent or energy stored in the apparatus, or being in contact with an environment of a particularly physical or chemical property.

5. The apparatus of claim 4, wherein the signal comprises an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

6. The apparatus of claim 5, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electrochemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, wherein the above stated properties can be static or dynamic and changing.

7. The apparatus of claim 1, wherein the decomposable material is in contact with an environment of a particular physical or chemical property which is a certain temperature, a certain humidity, a certain pH value, or a certain ionic strength.

8. The apparatus of claim 1, wherein the decomposable material decomposes in a period of time.

9. The apparatus of claim 8, wherein the period of time ranges from one second to two weeks.

10. The apparatus of claim 1, wherein the first sub-component is integrated inside the first micro device.

11. The apparatus of claim 10, wherein the first sub-component comprises a drug, a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a micro-injector, a signal transmitter, a signal generator, a friction sensor, an electrical charge sensor, a temperature sensor, a hardness detector, an acoustic wave generator, an optical wave generator, a heat generator, a micro refrigerator, or a charge generator.

12. The apparatus of claim 1, wherein the first sub-component is attached onto the surface of the first micro device.

13. The apparatus of claim 12, wherein the first sub-component comprises a drug, a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a micro-injector, a signal transmitter, a signal generator, a friction sensor, an electrical charge sensor, a temperature sensor, a hardness detector, an acoustic wave generator, an optical wave generator, a heat generator, a micro refrigerator, or a charge generator.

14. The apparatus of claim 1, wherein the decomposable material decomposes in the in vivo environment of a human being.

15. The apparatus of claim 14, wherein the in vivo environment is blood, stomach fluid, or urine.

16. The apparatus of claim 1, further comprising at least one more micro device which comprises a decomposable material that is the same as or different from the decomposable material of the first micro device.

17. The apparatus of claim 16, wherein the sub-component is positioned between two micro devices.

18. The apparatus of claim 17, wherein the sub-component is a drug, a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a micro-injector, a signal transmitter, a signal generator, a friction sensor, an electrical charge sensor, a temperature sensor, a hardness detector, an acoustic wave generator, an optical wave generator, a heat generator, a micro refrigerator, or a charge generator.

19. The apparatus of claim 16, wherein the sub-component is integrated inside one of the micro devices.

20. The apparatus of claim 19, wherein the sub-component comprises a drug, a voltage comparator, a four point probe, a calculator, a logic circuitry, a memory unit, a micro cutter, a micro hammer, a micro shield, a micro dye, a micro pin, a micro knife, a micro needle, a micro thread holder, micro tweezers, a micro optical absorber, a micro mirror, a micro wheeler, a micro filter, a micro chopper, a micro shredder, micro pumps, a micro absorber, a micro signal detector, a micro driller, a micro sucker, a micro tester, a micro container, a micro-injector, a signal transmitter, a signal generator, a friction sensor, an electrical charge sensor, a temperature sensor, a hardness detector, an acoustic wave generator, an optical wave generator, a heat generator, a micro refrigerator, or a charge generator.

21. The apparatus of claim 1, wherein the apparatus comprises one or more sub-components or one or more micro devices, and the sub-components and the micro devices are so interlaced that the apparatus decomposes into smaller pieces when one of the subcomponent and the micro device decompose or change its geometric parameter.

22. The apparatus of claim 1, wherein the apparatus can be decomposed to smaller pieces on the order of 0.1 micron in size.

23. The apparatus of claim 1, wherein the apparatus can be decomposed to smaller pieces smaller than 0.1 micron in size.

24. A nano-drug delivery apparatus, comprising a nano-drug and a micro device wherein the micro device comprises a decomposable material and the nano-drug is attached to or integrated into the micro device; wherein the apparatus comprises a layer with an interlaced structure, and the interlaced structure comprises straight-sided building blocks and is formed by at least two materials, one being the decomposable material, and the layer decomposes into smaller pieces upon the decomposition of the decomposable material; wherein the layer is included by the micro device, or comprises the first micro device and the nano-drug;

wherein the interlaced structure comprises at least two types of the building blocks, with one type of the building blocks surrounded by other types of the building blocks, and when one type of the building blocks decomposes or changes geometric parameter, the layer with the interlaced structure decomposes into smaller pieces.

25. The apparatus of claim 24, wherein the decomposable material comprises poly(lactide-co-glycolide), poly(lactide), poly(L-lactic acid), poly(D,L-lactic acid), polyglycolic acid, polyanhydride, poly(ortho ether), polyamino acid, engineered artificial protein, natural protein, biopolymer, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof.

26. The apparatus of claim 24, wherein the decomposable material is activated to decompose by a signal, an agent or an energy stored in the apparatus, or being in contact with an environment of a particularly physical or chemical property.

27. The apparatus of claim 26, wherein the signal comprises an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

28. The apparatus of claim 27, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, wherein the above stated properties can be static or dynamic and changing.

29. The apparatus of claim 26, wherein the decomposable material is in contact with an environment of a particular physical or chemical property which is a certain temperature, a certain humidity, a certain pH value, or a certain ionic strength.

30. The apparatus of claim 24, wherein the decomposing material decomposes in a period of time.

31. The apparatus of claim 30, wherein the period of time ranges from one second to two weeks.

32. The apparatus of claim 24, wherein the nano-drug is integrated into the micro device.

33. The apparatus of claim 24, further comprising at least one more nano-drug.

34. The apparatus of claim 33, further comprising at least one more micro device comprising a decomposable material.

35. The apparatus of claim 34, wherein the at least two nano-drugs are integrated in at least two different micro devices.

36. The apparatus of claim 24, further comprising a medical kit, a micro-disease detection system, or an auto-navigation system.

37. The apparatus of claim 36, wherein when the micro-disease detection system detects a disease, it sends a signal to trigger the decomposition of the decomposable material.

38. The apparatus of claim 37, wherein the signal comprises an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

39. The apparatus of claim 38, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electrochemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, wherein the above stated properties can be static or dynamic and changing.

40. The apparatus of claim 37, wherein the decomposable material is activated to decompose when receiving the signal from the micro-disease detection system.

41. The apparatus of claim 36, wherein the auto-navigating system navigates the apparatus to a lesion and the apparatus performs a treatment at the lesion.

42. The apparatus of claim 24, wherein the apparatus comprises one or more nano-drugs or one or more micro devices, and the sub-components and the micro devices are interlaced so that the apparatus decomposes into smaller pieces when one of the subcomponent and the micro device decompose or change its geometric parameter.

43. The apparatus of claim 24, wherein the apparatus can be decomposed to smaller pieces on the order of 0.1 micron in size.

44. The apparatus of claim 24, wherein the apparatus can be decomposed to smaller pieces on the order of below 0.1 micron in size.

45. A medical apparatus comprising at least two types of straight-sided building blocks connected together and forming an interlaced structure, wherein at least one type of the building blocks comprises a decomposable material at the molecular level, and is surrounded by the other building blocks each comprising a material that does or does not decompose at the molecular level, and the medical apparatus or the building blocks together disintegrates into much smaller pieces or molecules upon the decomposition of the at least one type of the building blocks.

46. The apparatus of claim 45, wherein at least one building block comprises a material that does not decompose at or to the molecular level.

47. The apparatus of claim 45, wherein the decomposable material comprises a protein, polypeptide, polysaccharide, polyester, polyorthoester, polycaprolactone, polydioxanone, an organic material, or a biological material.

48. The apparatus of claim 45, wherein the material that does not decompose at molecular level comprises poly (lactide-co-glycolide), poly(lactide), poly(L-lactic acid), poly(D,L-lactic acid), polyglycolic acid, polyanhydride, poly(ortho ether), polyamino acid, engineered artificial protein, natural protein, biopolymer, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a semiconductor material, an inorganic material, a biological material, or a composite thereof.

49. The apparatus of claim 45, wherein the decomposable material decomposes in vivo due to interaction with its surrounding environment.

50. The apparatus of claim 45, wherein the decomposable material decomposes in vivo after being trigger by a signal which comprises an electrical, magnetic, electromagnetic, thermal, optical, acoustical, biological, chemical, electromechanical, electro-chemical, electro-optical, electro-thermal, electro-chemical-mechanical, bio-chemical, bio-mechanical, bio-optical, bio-thermal, bio-physical, bio-electromechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

51. The apparatus of claim 50, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electrochemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, and each of the properties can be static or dynamic and changing.

52. The apparatus of claim 45, wherein the decomposable material completely decomposes or partially degrade in geometry within a period of time.

53. The apparatus of claim 52, wherein the period of time ranges from one second to two weeks.

54. The apparatus of claim 45, wherein the building blocks are interlaced so that the apparatus decomposes into smaller pieces when one of the subcomponent and the micro device decompose or change its geometric parameter.

55. The apparatus of claim 45, wherein the apparatus can be decomposed to smaller pieces on the order of 0.1 micron in size.

56. The apparatus of claim 45, wherein the apparatus can be decomposed to smaller pieces on the order of below 0.1 micron in size.

57. An apparatus for carrying a drug, comprising a first drug, an inner micro device comprising a first decomposable material packaging the first drug, a second drug, and an outer micro device encompassing the inner micro device and comprising a second decomposable material packaging the second drug, wherein the first drug is inside the inner micro device, and the second drug is positioned between the inner micro device and the outer micro device.

58. The apparatus of claim 57, wherein the first drug and the second drug are the same.

59. The apparatus of claim 57, wherein the first or second decomposable material comprises poly(lactide-co-glycolide), poly(lactide), poly(L-lactic acid), poly(D,L-lactic acid), polyglycolic acid, polyanhydride, poly(ortho ether), polyamino acid, engineered artificial protein, natural protein, biopolymer, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof.

60. The apparatus of claim 57, wherein the decomposable material in the outer micro device or the inner micro device is activated to decompose when a signal is applied to it.

61. The apparatus of claim 60, wherein the signal comprises an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

62. The apparatus of claim 61, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, wherein the above stated properties can be static or dynamic and changing.

63. The apparatus of claim 60, wherein the decomposable material decomposes in a desired period of time.

64. The apparatus of claim 63, wherein the desired period of time ranges from one second to two weeks.

65. The apparatus of claim 60, wherein the materials in the outer and inner micro devices decompose at a same time or different times.

66. The apparatus of claim 56, further comprising a medical kit, a micro-disease detection system, or an auto-navigation system, which is integrated in the inner micro device or the outer micro device.

67. The apparatus of claim 66, wherein the micro-disease detection system detects a disease and sends a signal to the inner or outer micro device to trigger the decomposition.

68. The apparatus of claim 67, wherein the signal comprises electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electro-mechanical-optical, bio-electro-thermal-optical, bio-electro-chemical-mechanical, physical or mechanical signal, or a combination thereof.

69. The apparatus of claim 68, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electro-chemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, wherein the above stated properties can be static or dynamic and changing.

70. The apparatus of claim 67, wherein the material in the inner or outer micro device is activated to decompose when the micro device receives the signal from the micro-disease detection system.

71. The apparatus of claim 66, wherein the auto-navigating system navigates the apparatus to a lesion and the apparatus performs a treatment in the lesion.

72. The apparatus of claim 66, wherein the drugs, micro device, and the medical kit, the micro-disease detection system, or the auto-navigation system are interlaced so that the apparatus decomposes into smaller pieces when at least one of the drugs, micro devices, the medical kit, the micro-disease detection system, and the auto-navigation system decomposes or changes its geometric parameter.

73. The apparatus of claim 57, wherein the drugs and micro device are so interlaced that the apparatus decomposes into smaller pieces when at least one of the drugs or micro devices decomposes or changes its geometric parameter.

74. The apparatus of claim 57, wherein the apparatus can be decomposed to smaller pieces on the order of 0.1 micron in size.

75. The apparatus of claim 57, wherein the apparatus can be decomposed to smaller pieces smaller than 0.1 micron in size.

76. A method for fabricating a decomposable apparatus, comprising:
providing a substrate;
optionally depositing a thin layer of material which can be removed later to separate the apparatus thus fabricated from the substrate;
depositing a first material onto the substrate, wherein the first material is decomposable;
patterning the first material with microelectronic technologies to form a recessed area in the first material;
depositing a second material onto the first material and the substrate, wherein the second material is different from the first material;
planarizing the second material to remove the second material from the top of the first material and stopping on the layer of the first material;
optionally repeating the patterning, depositing, and planarizing steps set forth above with one or more additional materials to give rise to the apparatus, wherein each of the one or more additional materials is different from the material deposited right before this one additional material;
optionally fabricating one or more additional components on the same substrate by repeating the depositing a new first material, patterning the new first material, depositing a new second material, or planarizing the new second material as describe above; and
removing the optional thin layer from the substrate to separate the apparatus and optional additional components from the substrate.

77. The method of claim 76, wherein the substrate comprises silicon, oxide, polysilicon, sapphire, a phosphate compound, a zirconium compound, or a calcium compound.

78. The method of claim 76, wherein the first material comprises a drug, a medical kit, a micro-disease detection system, or an auto-navigation system.

79. The method of claim 76, wherein the second material is also decomposable.

80. The method of claim 76, wherein the first decomposable material comprises poly(lactide-co-glycolide), poly(lactide), poly(L-lactic acid), poly(D,L-lactic acid), polyglycolic acid, polyanhydride, poly(ortho ether), polyamino acid, engineered artificial protein, natural protein, biopolymer, polyvinyl alcohol, polyethylene oxide, polymethacrylic acid, polyacrylic acid, polyethylene glycol, alginate, collagen, gelatin, hyaluronic acid, a magnesium metal, a magnesium alloy, a calcium phosphate ceramic, glass, a calcium compound, a phosphate compound, an oxide, a silicon, a polysilicon, a silicon nitride, a silicon oxynitride, silicon carbide, aluminum, aluminum alloy, copper, tungsten, silver, an organic material, a biological material, or a composite thereof.

81. The method of claim 76, wherein the patterning is carried out by lithography and etch processes.

82. The method of claim 76, wherein planarizing is carried out by polishing or etchback processes.

83. The method of claim 76, wherein the additional component or components comprise a voltage comparator, four-point probe, calculator, logic circuitry, memory unit, micro-cutter, micro-hammer, micro-shield, micro-dye, micro-pin, micro-knife, micro-needle, micro-thread holder, micro-tweezer, micro-optical absorber, micro-mirror, micro-wheeler, micro-filter, micro-chopper, micro-shredder, micro-pump, micro-absorber, micro-signal detector, micro-driller, micro-sucker, micro-tester, micro-container, micro-injector, signal transmitter, signal generator, friction sensor, electrical charge sensor, temperature sensor, hardness detector, acoustic wave generator, optical wave generator, micro-heater, heat generator, micro-refrigerator, and charge generator.

84. The method of claim 76, wherein the decomposable material is activated to decompose by a signal, an agent or an energy stored in the apparatus, or being in contact with an environment of a particularly physical or chemical property.

85. The method of claim 84, wherein the signal comprises an electrical, magnetic, electromagnetic, thermal, optical, acoustical, biological, chemical, electro-mechanical, electro-chemical, electro-optical, electro-thermal, electro-chemical-mechanical, bio-chemical, bio-mechanical, bio-optical, bio-thermal, bio-physical, bio-electro-mechanical, bio-electro-chemical, bio-electro-optical, bio-electro-thermal, bio-mechanical-optical, bio-mechanical thermal, bio-thermal-optical, bio-electro-chemical-optical, bio-electromechanical-optical, bio-electro-thermal-optical, bio-electrochemical-mechanical, physical or mechanical signal, or a combination thereof.

86. The method of claim 85, wherein the electrical property is surface charge, surface potential, resting potential, electrical current, electrical field distribution, electrical dipole, electrical quadruple, three-dimensional electrical or charge cloud distribution, electrical properties at telomere of DNA and chromosome, capacitance, or impedance; the thermal property is temperature or vibrational frequency; the optical property is optical absorption, optical transmission, optical reflection, optical-electrical property, brightness, or fluorescent emission; the chemical property is pH value, chemical reaction, bio-chemical reaction, bio-electrochemical reaction, reaction speed, reaction energy, speed of reaction, oxygen concentration, oxygen consumption rate, oxygen bonding site, oxygen bonding strength, local charge density due to oxygen atom and/or molecule properties and locations, local ionic density due to oxygen atom and/or molecule properties and locations, local electric field density due to oxygen atom and/or molecule properties and locations, ionic strength, catalytic behavior, chemical additives to trigger enhanced signal response, bio-chemical additives to trigger enhanced signal response, biological additives to trigger enhanced signal response, chemicals to enhance detection sensitivity, bio-chemicals to enhance detection sensitivity, biological additives to enhance detection sensitivity, or bonding strength; the physical property is density, shape, volume, or surface area; the biological property is surface shape, surface area, surface charge, surface biological property, surface chemical property, pH, electrolyte, ionic strength, resistivity, cell concentration, property relating to a bio-marker, or biological, electrical, physical or chemical property of solution; the acoustic property is frequency, speed of acoustic waves, acoustic frequency and intensity spectrum distribution, acoustic intensity, acoustical absorption, or acoustical resonance; the mechanical property is internal pressure, hardness, flow rate, viscosity, shear strength, elongation strength, fracture stress, adhesion, mechanical resonance frequency, elasticity, plasticity, or compressibility, wherein the above stated properties can be static or dynamic and changing.

87. The method of claim 84, wherein the decomposable material is in contact with an environment of a particular physical or chemical property which is a certain temperature, a certain humidity, a certain pH value, or a certain ionic strength.

88. The method of claim 76, wherein the decomposing material decomposes in a desired period of time.

89. The method of claim 88, wherein the desired period of time ranges from one second to two weeks.

90. The method of claim 76, wherein the second material can be etched back to the top of the first material, with the second material remaining in the portions of the recessed areas in the first material.

91. The method of claim 76, further comprising repeating the steps of etching an existing material, depositing another material, and planarizing the further deposited material to result in a decomposable apparatus comprising at least two layers.

92. The method of claim 76, wherein all components and apparatus are made of composite materials in which at least one material can be decomposed at or to the molecular level.

93. The method of claim 76, wherein the decomposing apparatus can be decomposed to smaller pieces on the order of 0.1 micron in size.

94. The method of claim 76, wherein the decomposing apparatus can be decomposed to smaller pieces smaller than 0.1 micron in size.

95. A method for fabricating a decomposable apparatus, comprising:
providing a substrate;
optionally depositing a thin layer of material which can be removed later to separate a material stack to be fabricated from the substrate;
depositing a first material onto the substrate, wherein the first material is decomposable;
patterning the first material with lithography and etch processes to form a recessed area in the first material;
depositing a second material onto the first material and the substrate, wherein the second material is different from the first material;
planarizing the second material from the top of the first material and stopping on the layer of the first material;
optionally repeating the patterning, depositing, and planarizing steps set forth above with one or more additional materials to build additional features, thus giving rise to the decomposable apparatus, wherein each of the one or more additional materials is different from the material deposited right before this one additional material;
optionally repeating the depositing, patterning, depositing, or planarizing to fabricate one or more additional components which may or may not be connected to the apparatus; and
removing the optional thin layer to separate the apparatus and optional additional components from the substrate.

96. The method of claim 95, wherein the additional components comprise of voltage comparators, four-point probes, calculators, logic circuitries, memory units, micro-cutters, micro-hammers, micro-shields, micro-dyes, micro-pins, micro-knives, micro-needles, micro-thread holders, micro-tweezers, micro-optical absorbers, micro-mirrors, micro-wheelers, micro-filters, micro-choppers, micro-shredders, micro-pumps, micro-absorbers, micro-signal detectors, micro-drillers, micro-suckers, micro-testers, micro-containers, micro-injectors, signal transmitters, signal generators, friction sensors, electrical charge sensors, temperature sensors, hardness detectors, acoustic wave generators, optical wave generators, micro-heaters, heat generators, micro-refrigerators, and charge generators.

97. The method of claim 95, wherein all components and apparatus are made of composite materials in which at least one material can be decomposed at or to the molecular level.

98. The method of claim 95, wherein the apparatus can be decomposed to smaller pieces on the order of 0.1 micron in size.

99. The method of claim 95, wherein the apparatus can be decomposed to smaller pieces on the order of below 0.1 micron in size.

100. The apparatus of claim 1, wherein at least one of the building blocks is cube-shaped.

* * * * *